(12) United States Patent
Horie et al.

(10) Patent No.: US 12,144,576 B2
(45) Date of Patent: Nov. 19, 2024

(54) TACTILE PRESENTATION APPARATUS AND TACTILE PRESENTATION SYSTEM

(71) Applicant: Sony Corporation, Tokyo (JP)

(72) Inventors: Ryuta Horie, Saitama (JP); Kazuo Hongo, Chiba (JP); Satoko Nagakari, Chiba (JP); Ryo Terasawa, Tokyo (JP); Yasunori Kawanami, Tokyo (JP)

(73) Assignee: SONY CORPORATION, Tokyo (JP)

( * ) Notice: Subject to any disclaimer, the term of this patent is extended or adjusted under 35 U.S.C. 154(b) by 1127 days.

(21) Appl. No.: 16/969,194

(22) PCT Filed: Jan. 21, 2019

(86) PCT No.: PCT/JP2019/001657
§ 371 (c)(1),
(2) Date: Aug. 12, 2020

(87) PCT Pub. No.: WO2019/163359
PCT Pub. Date: Aug. 29, 2019

(65) Prior Publication Data
US 2020/0405426 A1    Dec. 31, 2020

(30) Foreign Application Priority Data

Feb. 20, 2018  (JP) ................................ 2018-027903

(51) Int. Cl.
*A61B 34/00*  (2016.01)
*A61B 34/35*  (2016.01)
(Continued)

(52) U.S. Cl.
CPC .............. *A61B 34/76* (2016.02); *A61B 34/35* (2016.02); *A61B 34/74* (2016.02); *A61B 34/77* (2016.02);
(Continued)

(58) Field of Classification Search
CPC ......... A61B 34/76; A61B 34/35; A61B 34/74; A61B 34/77; A61B 2034/741; B25J 9/1694; G06F 3/016
See application file for complete search history.

(56) References Cited

U.S. PATENT DOCUMENTS 9,742,254 B1    8/2017  Choi et al.
9,849,595 B2 *  12/2017  Wang .................... B25J 13/025
(Continued)

FOREIGN PATENT DOCUMENTS

CN    104127245 A    11/2014
CN    104739519 A    7/2015
(Continued)

OTHER PUBLICATIONS

Extended European search report issued on Jan. 25, 2021, in corresponding European patent Application No. 19757817.2, 8 pages.
(Continued)

*Primary Examiner* — John A Tweel, Jr.
(74) *Attorney, Agent, or Firm* — XSENSUS LLP

(57) ABSTRACT

A tactile presentation apparatus including: an operation unit operated by a user; a vibration unit that presents a vibration of an operation target of the operation unit; a contact unit that transmits the vibration by the vibration unit to the user; and an installation unit coupled to the operation unit, over the contact unit provided via an elastic body.

18 Claims, 29 Drawing Sheets

(51) Int. Cl.
    *B25J 9/16*           (2006.01)
    *G06F 3/01*         (2006.01)

(52) U.S. Cl.
    CPC ............ *B25J 9/1694* (2013.01); *G06F 3/016* (2013.01); *A61B 2034/741* (2016.02)

(56) References Cited

U.S. PATENT DOCUMENTS

| | | | |
|---|---|---|---|
| 10,990,179 B2 * | 4/2021 | Suzuki | .................... G06F 3/016 |
| 11,049,674 B2 * | 6/2021 | Lane | .................... H01H 13/705 |
| 11,538,315 B2 * | 12/2022 | Suzuki | .................... A61B 34/37 |
| 2007/0091063 A1 | 4/2007 | Nakamura | |
| 2011/0057888 A1 | 3/2011 | Kim et al. | |
| 2014/0070667 A1 | 3/2014 | Oh et al. | |
| 2014/0152148 A1 | 6/2014 | Oh et al. | |
| 2017/0228028 A1 | 8/2017 | Nakamura | |
| 2017/0293359 A1 | 10/2017 | Ikuta et al. | |
| 2018/0368931 A1 * | 12/2018 | Hongo | .................... A61B 34/76 |

FOREIGN PATENT DOCUMENTS

| | | |
|---|---|---|
| CN | 105404156 A | 3/2016 |
| EP | 1876505 A1 | 1/2008 |
| JP | 62-208881 A | 9/1987 |
| JP | 2000-137576 A | 5/2000 |
| JP | 2014-024127 A | 2/2014 |
| JP | 2015-116660 A | 6/2015 |
| KR | 2011-0047917 A | 5/2011 |
| WO | 2012/105592 A1 | 8/2012 |
| WO | 2017/130562 A1 | 8/2017 |
| WO | 2017/162586 A1 | 9/2017 |
| WO | 2018/216780 A1 | 11/2018 |

OTHER PUBLICATIONS

International Search Report and Written Opinion mailed on Apr. 16, 2019 for PCT/JP2019/001657 filed on Jan. 21, 2019, 9 pages including English Translation of the International Search Report.

* cited by examiner

[ FIG. 29 ]
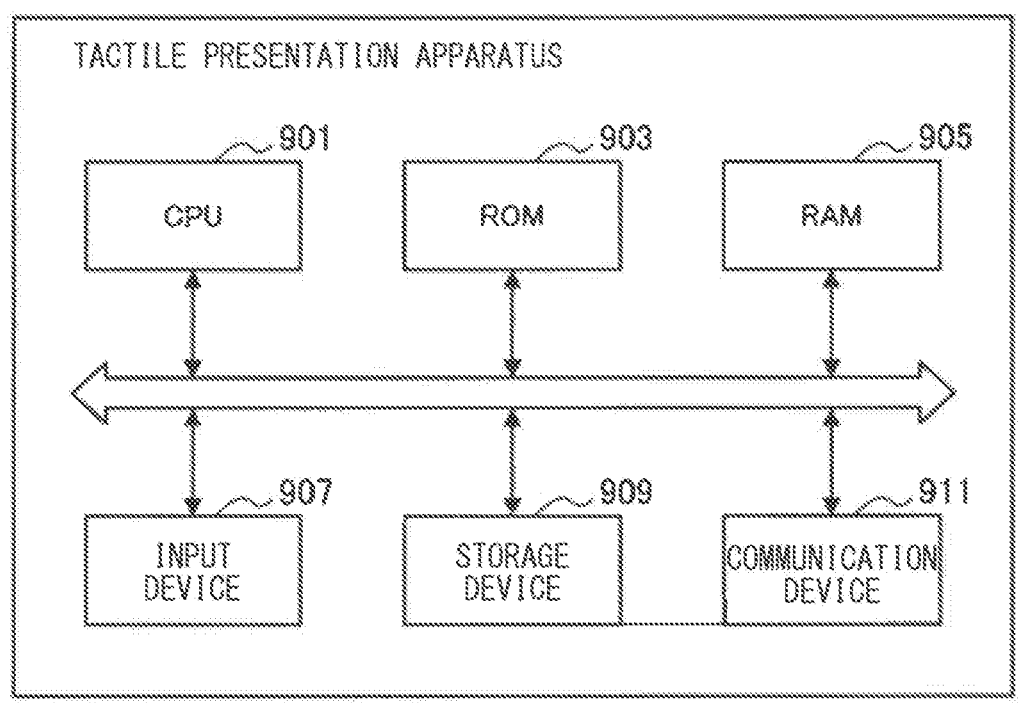

TACTILE PRESENTATION APPARATUS AND TACTILE PRESENTATION SYSTEM

CROSS-REFERENCE TO RELATED APPLICATIONS

The present application is based on PCT filing PCT/JP2019/001657, filed Jan. 21, 2019, which claims priority to JP 2018-027903, filed Feb. 20, 2018, the entire contents of each are incorporated herein by reference.

TECHNICAL FIELD

The present disclosure relates to a tactile presentation apparatus and a tactile presentation system.

BACKGROUND ART

In recent years, as a surgical system to be used when performing endoscopic surgery, a master-slave-based system is known which enables an approach to an affected area without making a large incision in a patient's body. In such a system, when an operator (user) such as a doctor operates a master apparatus provided with an input interface, a slave apparatus provided with medical surgical instruments such as forceps or tweezers is remotely operated in accordance with force of input operations of the operator measured by a force sensor provided in the master apparatus. The slave apparatus is configured as, for example, an arm apparatus with a surgical instrument being held at a tip end thereof, and is able to change the position or posture of the surgical instrument in an abdominal cavity.

In such a system, in a case where a tactile sense at the time when the surgical instrument comes into contact with the patient is not transmitted to the operator, the operator may not be aware that the surgical instrument is in contact with the patient, which may possibly cause damage to a biological tissue of the patient. Therefore, it is desirable that the tactile sense at the time when the surgical instrument comes into contact with the patient be transmitted to the operator. Examples of a method for transmitting to the operator the tactile sense at the time when the surgical instrument comes into contact with the patient include a method in which a sensor that measures the tactile sense is provided in the slave apparatus and sends information regarding the tactile sense measured by this sensor to a side of the master apparatus to transmit the tactile sense to the operator by a vibration, or the like. In this regard, PTL 1 listed below discloses a pressure sense/tactile sense presentation apparatus that expresses, as an expression of operating status, a pseudo-pressure sense/tactile sense by using a vibration of a vibratory actuator such as a voice coil motor.

CITATION LIST

Patent Literature

PTL 1: Japanese Unexamined Patent Application Publication No. H08-254472

SUMMARY OF THE INVENTION

Problem to be Solved by the Invention

However, in the method of PTL 1 described above, in a case where the pressure sense/tactile presentation apparatus is mounted on the master apparatus, the vibration of the vibratory actuator may be possibly transmitted to the force sensor of the master apparatus. Such a vibration of the vibratory actuator may serve as a noise in control of the master-slave system, and may cause an adverse effect.

Therefore, the present disclosure proposes a novel and improved tactile presentation apparatus and tactile presentation system that make it possible to reduce a noise to be transmitted to a force sensor.

Means for Solving the Problem

According to the present disclosure, there is provided a tactile presentation apparatus including: an operation unit operated by a user; a vibration unit that presents a vibration of an operation target of the operation unit; a contact unit that transmits the vibration by the vibration unit to the user; and an installation unit coupled to the operation unit, over the contact unit provided via an elastic body.

In addition, according to the present disclosure, there is provided a tactile presentation system including: a first information processor provided with a tactile presentation apparatus that presents to a user a first signal, as a tactile sense, related to a vibration of an operation target received from a slave apparatus, in which the first information processor functions as a master apparatus that transmits to the slave apparatus a second signal in which a vibration noise estimated on a basis of the first signal is removed from force applied by the user; and a second information processor functioning as the slave apparatus that transmits to the first information processor the first signal measured when being driven on a basis of the second signal received from the first information processor.

Effect of the Invention

As described above, according to the present disclosure, it is possible to reduce a noise to be transmitted to a force sensor.

It is to be noted that the above-mentioned effects are not necessarily limitative; in addition to or in place of the above effects, there may be achieved any of the effects described in the present specification or other effects that may be grasped from the present specification.

BRIEF DESCRIPTION OF THE DRAWINGS

FIG. 29 is a block diagram illustrating a hardware configuration example of the tactile presentation apparatus according to an embodiment of the present disclosure.

MODES FOR CARRYING OUT THE INVENTION

Figure 1:
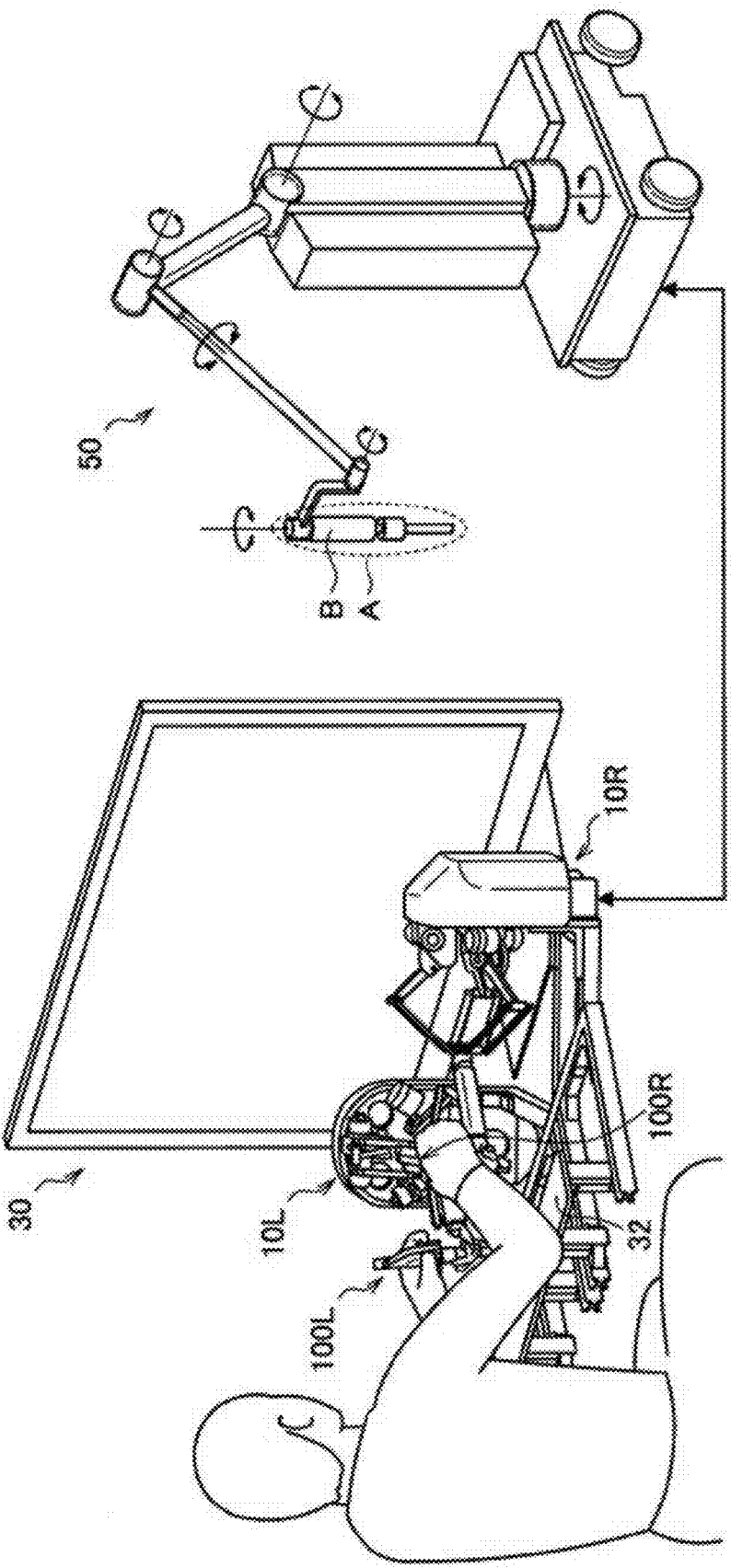
FIG. 1 is an explanatory diagram illustrating an overview of a tactile presentation system according to an embodiment of the present disclosure.

Hereinafter, description is given in detail of preferred embodiments of the present disclosure with reference to the accompanying drawings. It is to be noted that, in the present specification and drawings, repeated description is omitted for components substantially having the same functional configuration by assigning the same reference numerals.

It is to be noted that description is given in the following order.
1. Overview of Tactile Presentation System
2. Master Apparatus of Embodiment of Present Disclosure
 2.1. External Configuration Example of Master Apparatus
 2.2. Internal Configuration Example of Master Apparatus
3. First Embodiment
3.1. External Configuration Example of Operation Apparatus
3.2. Operation Example
3.3. Modification Examples
4. Second Embodiment
 4.1. External Configuration Example of Operation Apparatus
 4.2. Operation Example
 4.3. Modification Examples
5. Hardware Configuration
6. Conclusion

1. OVERVIEW OF TACTILE PRESENTATION SYSTEM

Hereinafter, description is given of an overview of a tactile presentation system according to an embodiment of the present disclosure with reference to FIG. 1. It is to be noted that the description of the overview of the tactile presentation system according to an embodiment of the present disclosure is given by exemplifying a master-slave-based medical robotic system.

FIG. 1 is an explanatory diagram illustrating an overview of the tactile presentation system according to an embodiment of the present disclosure. As illustrated in FIG. 1, the tactile presentation system is roughly configured by a master apparatus 10 (10R and 10L) and a slave apparatus 50. The master apparatus 10 is an apparatus provided with an input interface to be operated by an operator such as a doctor (hereinafter, also referred to as a user). In addition, the slave apparatus 50 is an apparatus provided with medical surgical instruments such as forceps or tweezers to be remotely operated in accordance with operations of a user on the master apparatus 10.

The tactile presentation system employs bilateral control as an example. The bilateral control refers to a feedback control that conforms the input interface to a position of the surgical instrument as well as a status of force, between the master apparatus 10 and the slave apparatus 50. For example, when the user operates the input interface, the surgical instrument moves in accordance with this operation. When the surgical instrument moves to come into contact with a patient, force upon the contact is fed back to the input interface.

It is to be noted that the master apparatus 10 and the slave apparatus 50 are coupled to each other by any communication method. For example, the master apparatus 10 and the slave apparatus 50 are coupled to each other by wired communication or wireless communication. In addition, for example, the master apparatus 10 and the slave apparatus 50 may be configured to communicate directly, or may be configured to communicate via a network (or another apparatus).

(1) Master Apparatus 10

The master apparatus 10 is an information processor (first information processor) having functions of drive control of the slave apparatus 50 and presentation to the user of a vibration signal (first signal) measured by a sensor of the slave apparatus 50. The master apparatus 10 is, for example, an apparatus having one or two or more joints including a passive joint and a link coupled to the joints (apparatus having a link mechanism including a passive joint). It is to be noted that the passive joint is a joint that is not driven by a motor, an actuator, or the like.

As illustrated in FIG. 1, the master apparatus 10 is provided with an operation apparatus 100 (100R and 100L) to be grasped and operated by the user. The operation apparatus 100 corresponds to a tactile presentation apparatus according to an embodiment of the present disclosure. In addition, a monitor 30 on which a surgical field is displayed is coupled to the master apparatus 10, and a support rest 32 on which a user places both arms or both elbows is provided. It is to be noted that the master apparatus 10 is configured by the master apparatus 10R for the right hand and the master apparatus 10L for the left hand. Further, the master apparatus 10R for the right hand is provided with the operation apparatus 100R for the right hand, and the master apparatus 10L for the left hand is provided with the operation apparatus 100L for the left hand.

The user places both arms or both elbows on the support rest 32, and grasps the operation apparatuses 100R and 100L with the right hand and the left hand, respectively. In this state, the user operates the operation apparatuses 100R and 100L while viewing the monitor 30 on which the surgical field is displayed. The user may remotely operate the position or orientation of surgical instruments attached to the slave apparatus 50 by displacing positions and orientations of the operation apparatuses 100R and 100L, or may perform a grasping motion with each of the surgical instruments.

(2) Slave Apparatus 50

The slave apparatus 50 is an information processor (second information processor) that presents, to the master apparatus 10, an affected area (hereinafter, also referred to as a target) of a patient in the operation as well as force and a vibration at the time when a portion of the slave apparatus 50 for contact comes into contact with the target. The slave apparatus 50 is, for example, an apparatus having one or two or more active joints and a link coupled to the active joints (apparatus having a link mechanism including the active joints), for movement in accordance with motion of the master apparatus 10. It is to be noted that the active joint is a joint driven by a motor, an actuator, or the like.

In the slave apparatus 50, a tip end part (A illustrated in FIG. 1) of an arm illustrated in FIG. 1 is provided with various sensors (e.g., an origin sensor, a Limit sensor, an encoder, a microphone, an acceleration sensor, etc.). In addition, the tip end part of the arm of the slave apparatus 50 is provided with a force sensor (B illustrated in FIG. 1). The force sensor measures force applied to the tip end part of the arm when the tip end part of the arm comes into contact with the patient. It is to be noted that a location where the above-mentioned various sensors are provided is not particularly limited; the various sensors may be provided at any location of the tip end part of the arm.

The slave apparatus 50 is provided with, for example, motion sensors for measuring motions of the active joints, at positions corresponding to the respective active joints. Examples of the motion sensor include an encoder. In addition, the slave apparatus 50 is provided with, for example, drive mechanisms for driving the active joints, at positions corresponding to the respective active joints. Examples of the drive mechanism include a motor and a driver.

It is to be noted that the embodiment of the present disclosure may be applied to a virtual reality environment. For example, when the master apparatus 10 is operated, an image indicating a virtual environment on a side of the slave apparatus 50 may be displayed on the monitor 30 to allow the user to operate the master apparatus 10 on the basis of the image.

The description has been given above of an overview of the tactile presentation system according to an embodiment of the present disclosure with reference to FIG. 1. Consequently, description is given of the master apparatus of an embodiment of the present disclosure.

2. MASTER APPARATUS OF EMBODIMENT OF PRESENT DISCLOSURE

Description is given in more detail of the master apparatus 10 of an embodiment of the present disclosure with reference to FIGS. 2 to 6.

2.1. External Configuration Example of Master Device

Figure 2:
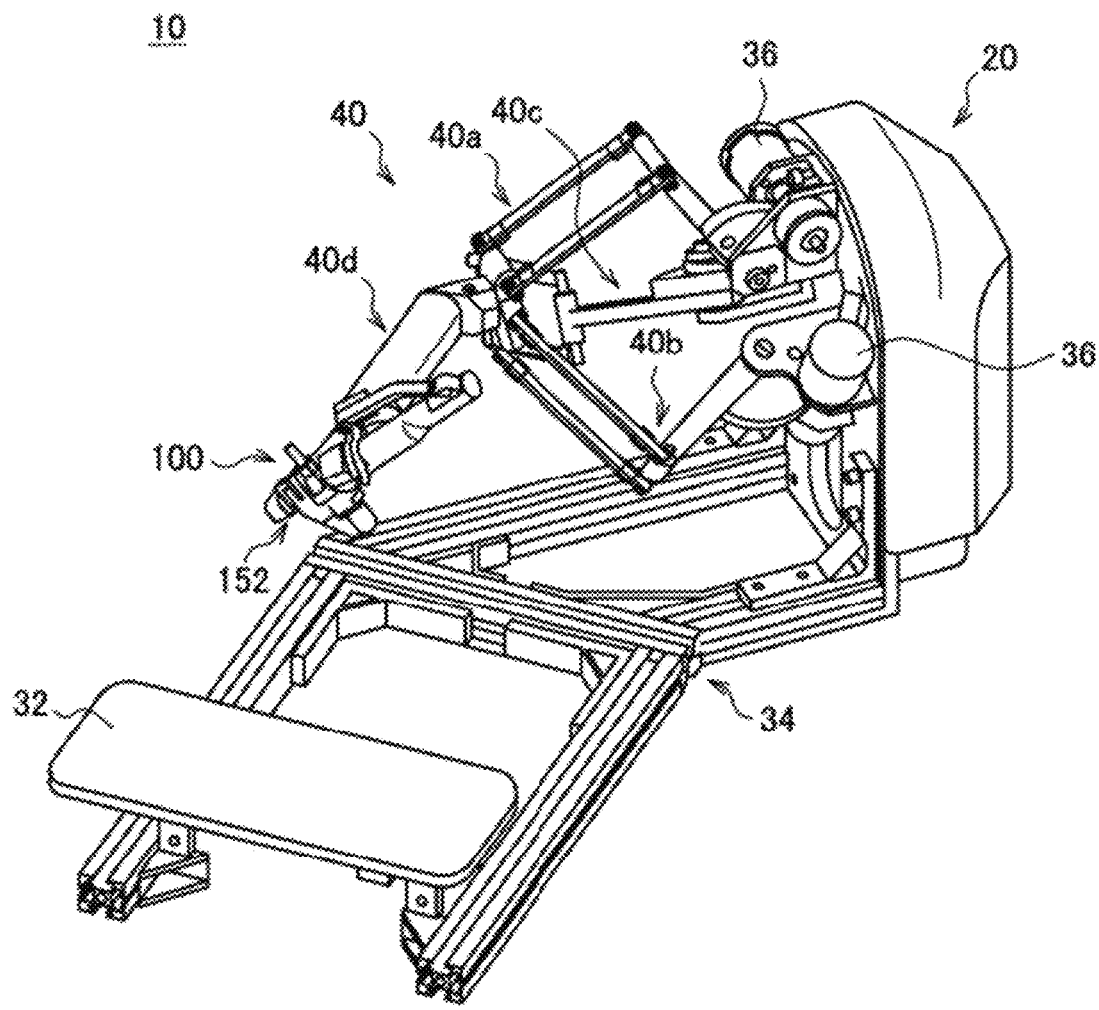
FIG. 2 is a block diagram illustrating an external configuration example of a master apparatus according to the same embodiment.

First, description is given of an external configuration example of the master apparatus 10 with reference to FIG. 2. FIG. 2 is an explanatory diagram illustrating the external configuration example of the master apparatus 10 according to an embodiment of the present disclosure.

The master apparatus 10 illustrated in FIG. 2 is provided with a support arm part 40, a body part 20, a base part 34, and an operation apparatus 100. The base part 34 is a pedestal part of the master apparatus 10, and may be configured by combining a frame material made of aluminum, for example. However, the configuration of the base part 34 is not limited to such an example. The support rest 32 is attached to the base part 34. The user operates the operation apparatus 100, with elbows or arms placed on the support rest 32, thereby making it possible to achieve stability of the operation. It is to be noted that the support rest 32 neither needs to be attached to the base part 34 nor needs to be included as a component of the master apparatus 10.

The support arm part 40 is supported by the body part 20 on a base end side. The operation apparatus 100 is attached to tip end side of the support arm part 40. The support arm part 40 includes a first arm part 40a, a second arm part 40b, a third arm part 40c, and a fourth arm part 40d. Each tip end side of the first arm part 40a, the second arm part 40b and the third arm part 40c is linked to the fourth arm part 40d, and the base end side is linked to the body part 20. The body part 20 is provided with three motors 36 (one of these not illustrated) that control rotation of respective linkage parts between the first arm part 40a, the second arm part 40b and the third arm part 40c, and the body part 20.

The first arm part 40a, the second arm part 40b, and the third arm part 40c are each configured by a plurality of link parts pivotally linked together in series. In addition, respective linkage parts between the first arm part 40a, the second arm part 40b and the third arm part 40c, and the fourth arm part 40d are also pivotally linked together. Further, the respective linkage parts between the first arm part 40a, the second arm part 40b and the third arm part 40c, and the body part 20 are also pivotally linked together.

The plurality of these link parts or the linkage parts of the arm parts serve as joint parts, and angles of the respective link parts or arm parts may freely change about the joint parts. This may freely change a position, in space, of the operation apparatus 100 attached to the tip end side of the support arm part 40. In addition, the fourth arm part 40d is configured by a plurality of linked arms, with each of the arms being axially rotatable. This may freely change orientation of the operation apparatus 100 attached to the tip end side of the support arm part 40.

Each of the linkage parts between the first arm part 40a, the second arm part 40b and the third arm part 40c, and the body part 20 is provided with an encoder for detecting a rotational angle of each of the arm parts. In addition, the fourth arm part 40d is provided with a plurality of encoders for detecting axis rotational angles of the respective arms. The encoder is an example of a sensor that detects a rotational angle, and may be replaced by another sensor. Signals indicating rotational angles detected by these encoders are transmitted to a control unit described later included in the master apparatus 10.

The operation apparatus 100 functions as a grasping interface for operating a surgical instrument supported by the slave apparatus 50. The user changes the position and the orientation of the operation apparatus 100 to thereby change a posture of the support arm part 40 and to change the rotational angle of the joint part and the axis rotational angle of the arm. The coupling part between the operation apparatus 100 and the fourth arm part 40d is provided with a force sensor 152. Such a force sensor 152 detects force inputted to the operation apparatus 100 by the user.

It is to be noted that the support arm part 40 including a rotational angle sensor that detects the rotational angle of the joint part and the axis rotational angle of the arm may be configured using an existing known support arm apparatus, and thus detailed description of the configuration of the support arm part 40 is omitted.

The description has been given above, with reference to FIG. 2, of the external configuration example of the master apparatus 10 according to an embodiment of the present disclosure.

2.2. Internal Configuration Example of Master Apparatus

Figure 3:
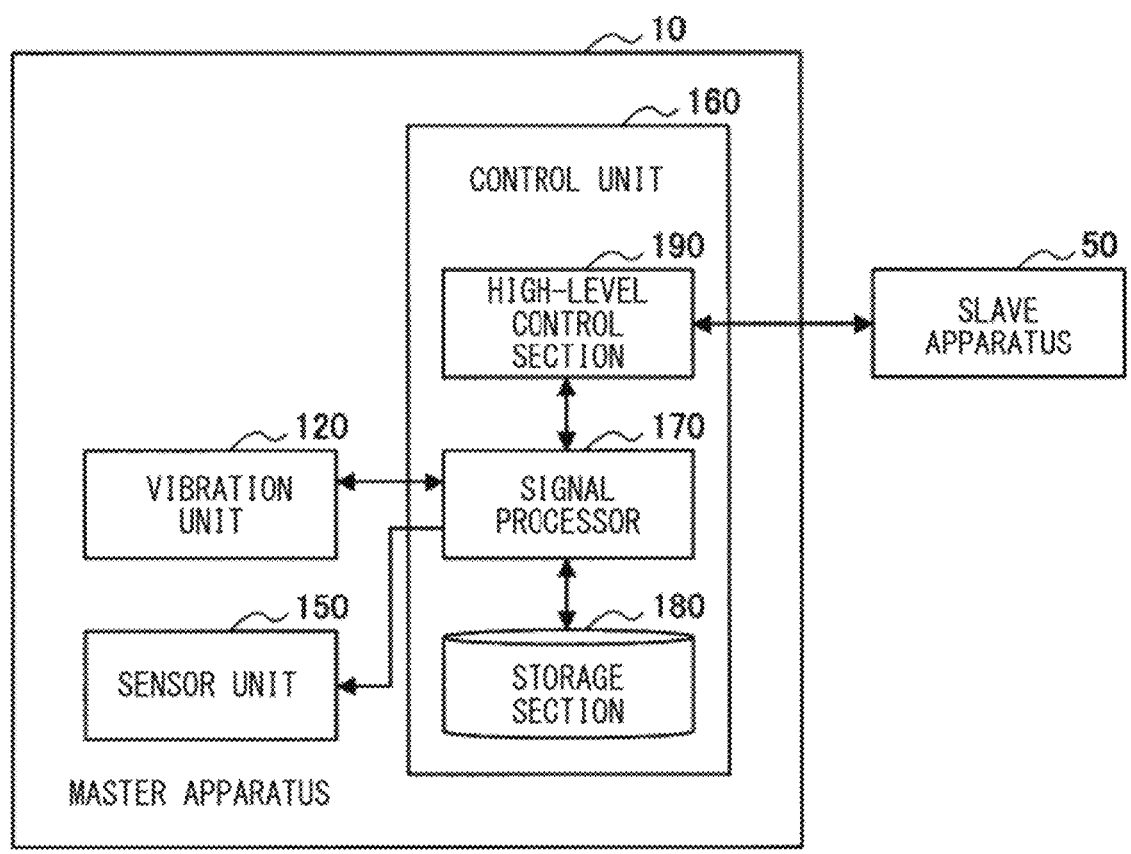
FIG. 3 is an explanatory diagram illustrating an internal configuration example of the master apparatus according to the same embodiment.

Next, description is given of an internal configuration example of the master apparatus 10 of an embodiment of the present disclosure with reference to FIGS. 3 to 6. FIG. 3 is a block diagram illustrating an internal configuration example of the master apparatus 10 according to an embodiment of the present disclosure. As illustrated in FIG. 3, the master apparatus 10 is configured by a vibration unit 120, a sensor unit 150, and a control unit 160.

(1) Vibration Unit 120

The vibration unit 120 is a vibration device for presenting a vibration of an operation target of the operation apparatus 100, and is included in the operation apparatus 100. For example, the vibration unit 120 vibrates in accordance with an input from a signal processor 170 based on a vibration generated by the operation target touching an object. It is to be noted that, in a first embodiment of the present disclosure, a voice coil motor (VCM: Voice Coil Motor) type vibratory actuator is used as the vibration unit 120; however, another vibration device may be adopted. For example, an LRA (Linear Resonant Actuator) or a piezoelectric element may be used as the vibrating device.

(2) Sensor Unit 150

A sensor unit 150 has a function of measuring information for performing drive control of the slave apparatus 50 and force sense presentation. For example, the sensor unit 150 includes the force sensor 152 (torque sensor) and a rotational angle sensor. As described above with reference to FIG. 2, the force sensor 152 is provided, for example, on the coupling part between the support arm part 40 and the operation apparatus 100 attached to the tip end of the support arm part 40, and measures force acting in three axis directions orthogonal to one another. That is, the force sensor 152 measures force inputted to the operation apparatus 100 by the user. In addition, the rotational angle sensor is provided at a plurality of joint parts of the support arm part 40, and measures a rotation angle of each of the joint parts. The rotational angle sensor may be, for example, an encoder.

It is to be noted that the force sensor 152 attempts to measure force of the user applied when the user operates the operation apparatus 100. However, the force measured by the force sensor 152 includes, in addition to the force of the user, gravity generated by self-weight of the operation apparatus 100 and inertia force generated by movement of the operation apparatus 100. In addition, the force measured by the force sensor 152 may include the vibration generated by the vibration unit 120 as a noise in some cases. As described above, the force measured by the force sensor 152, which includes at least one of gravity, inertia force or noise, in addition to the force of the user, is also referred to below as external force. In addition, hereinafter, description of embodiments of the present disclosure is given, on the assumption that the external force includes the force of the user, gravity, inertia force, and a noise.

The information measured by the sensor unit 150 as described above is outputted to the control unit 160.

(3) Control Unit 160

The control unit 160 has a function of controlling operations of the slave apparatus 50. For example, the control unit 160 controls a posture of the arm of the slave apparatus 50 on the basis of information on the rotational angle detected by the encoder included in the master apparatus 10 to change the position and the orientation of the surgical instrument supported by the slave apparatus 50. At this time, the control unit 160 detects external force acting on a surgical instrument of the slave apparatus 50, and applies reaction force to the motion of the operation apparatus 100 operated by the user by performing drive control of the three motors 36 (one of these not illustrated) on the basis of the external force to present to the user a force sense for the movement operation of the operation apparatus 100.

In addition, the control unit 160 acquires a signal indicating an operation amount of a grasping motion from the operation apparatus 100 by the user performing the grasping motion of the operation apparatus 100, and causes the surgical instrument attached to the slave apparatus 50 to perform the grasping motion on the basis of the signal. At this time, the control unit 160 may detect reaction force for the time of the grasping motion of the surgical instrument attached to the slave apparatus 50 and may perform drive control of an unillustrated motor included in the operation apparatus 100 on the basis of the reaction force to thereby present to the user a force sense for the grasping motion of the operation apparatus 100.

In addition, the control unit 160 has a function of controlling processing of transmitting a vibration measured by the slave apparatus 50 to the user. In order to achieve such processing, the control unit 160 according to an embodiment of the present disclosure includes the signal processor 170, a storage section 180, and a high-level control section 190, as illustrated in FIG. 3.

(Signal Processor 170)

The signal processor 170 has a function of controlling the vibration of the vibration unit 120 on the basis of a signal received from the slave apparatus 50. For example, the signal processor 170 receives the vibration signal measured by the sensor of the slave apparatus 50 via the high-level control section 190 described later, performs signal processing for removing a noise from the vibration signal, and controls the vibration unit 120 to vibrate on the basis of the processed vibration signal.

In addition, the signal processor 170 has a function of controlling processing of outputting force corresponding to the force measured by the sensor unit 150 to the high-level control section 190. For example, the signal processor 170 removes a component of the vibration presented by the vibration unit 120 from the external force measured by the force sensor 152.

Figure 4:
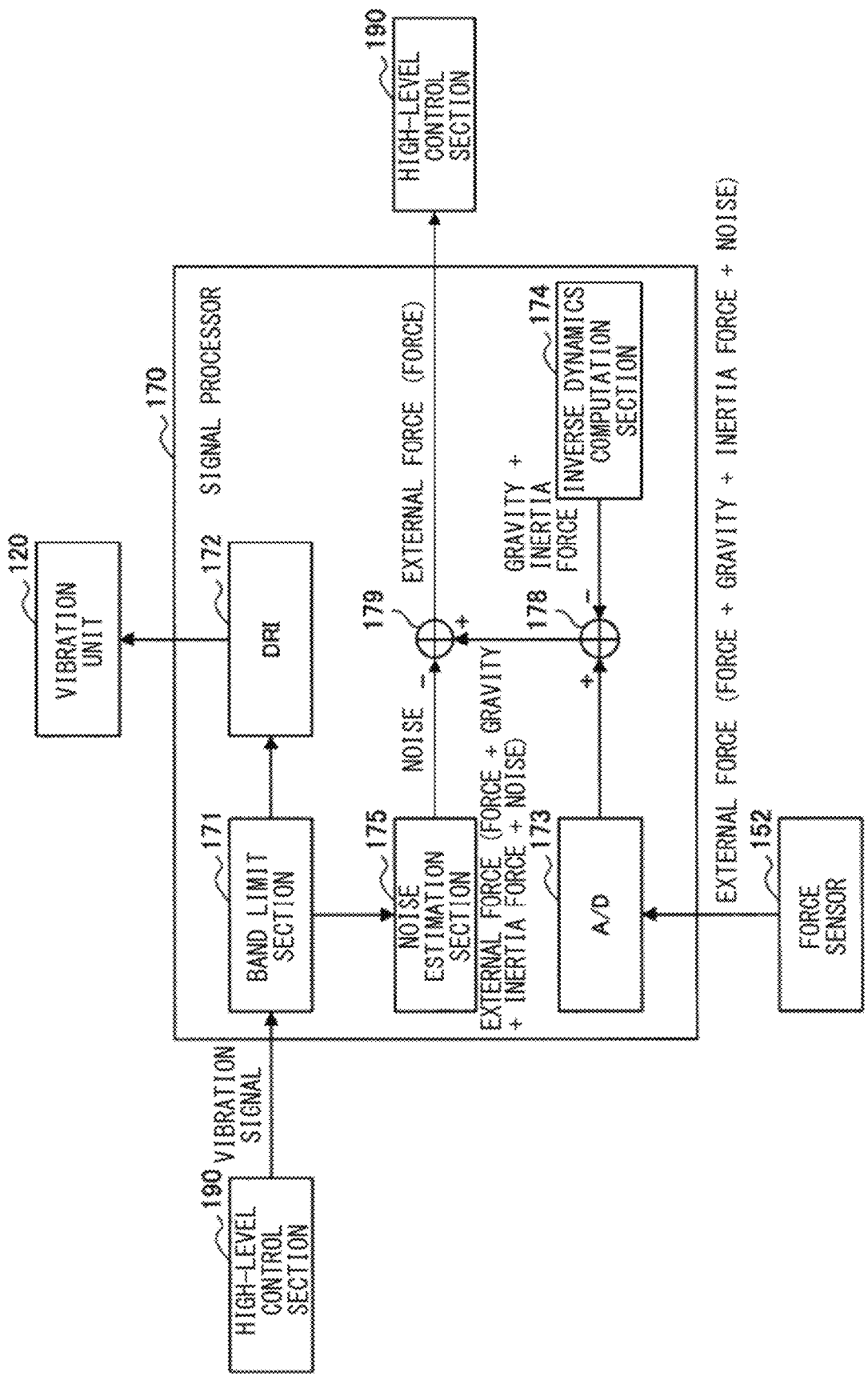
FIG. 4 is a block diagram illustrating a configuration example of a signal processor according to the same embodiment.
Figure 5:
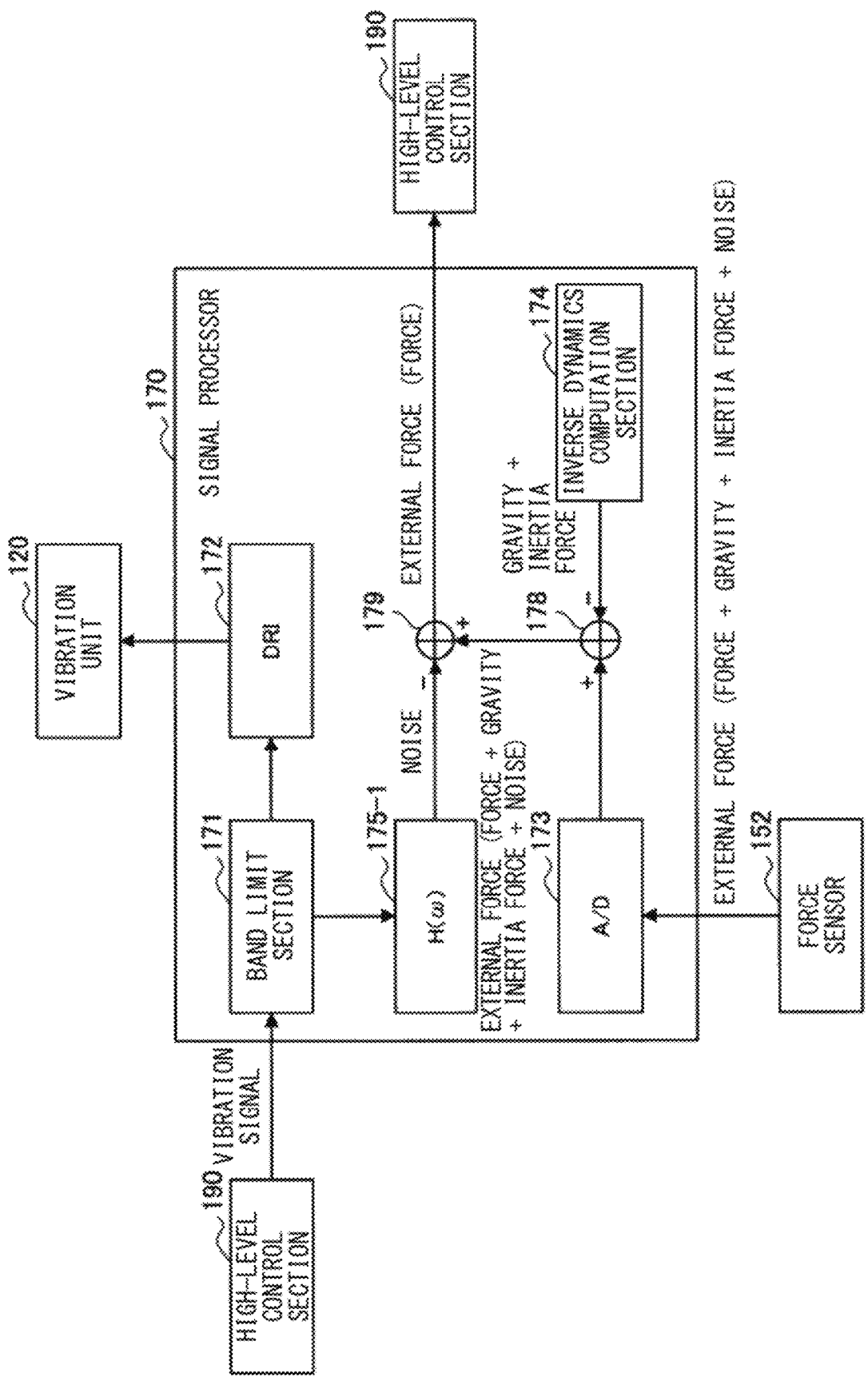
FIG. 5 is a block diagram illustrating a configuration example of the signal processor according to the same embodiment.
Figure 6:
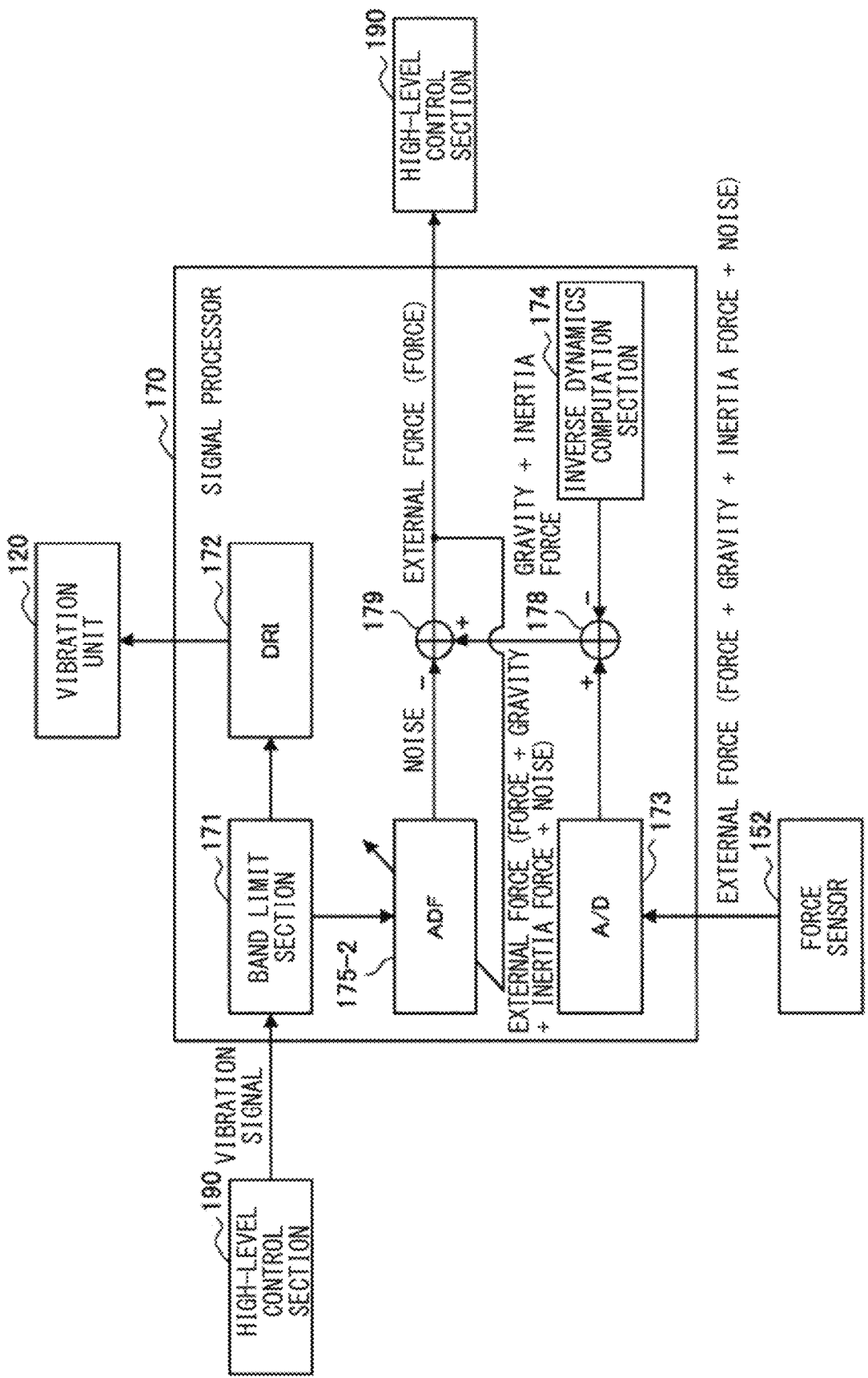
FIG. 6 is a block diagram illustrating a configuration example of the signal processor according to the same embodiment.

Description is now given of a configuration example of the signal processor 170 of an embodiment of the present disclosure with reference to FIGS. 4 to 6. FIGS. 4 to 6 are each a block diagram illustrating a configuration example of the signal processor 170 according to embodiments of the present disclosure. In order to achieve the functions described above, the signal processor 170 according to an embodiment of the present disclosure is configured as a signal processing circuit including a band limit section 171, a DRI (DRIVER) 172, an A/D 173, an inverse dynamics computation section 174, a noise estimation section 175, an adder 178, and an adder 179, as illustrated in FIG. 4.

Band Limit Section 171

The band limit section 171 has a function of removing a specific band from an input signal. For example, the band limit section 171 uses a filter to remove a low-frequency component which, as a vibration noise, may possibly affect the force sensor 152 of the master apparatus 10; the band limit section 171 removes a frequency component corresponding to a vibration such as a sound not perceived by the user as a tactile sense or a predetermined frequency component stored in advance, from the vibration signal. More specifically, the band limit section 171 filters the input signal to remove the predetermined frequency band component. More specifically, for example, the band limit section 171 uses a high-pass filter (HPF: High-Pass Filter), which passes only a high-range signal while blocking a low-range signal, to block a vibration signal equal to or less than a predetermined frequency, thereby removing a specific band from the input signal. The predetermined frequency, as used herein, refers to a lower limit value of the low-frequency component that may possibly affect, as the vibration noise, the force sensor 152 of the master apparatus 10. For example, the predetermined frequency may be about 30 Hz. It is to be noted that the above-described predetermined frequency may be registered in advance in the storage section 180.

In addition, the band limit section 171 uses, for example, a low-pass filter (LPF: Low-Pass Filter), which passes only a low-range signal while blocking a high-range signal, to block a vibration signal equal to or more than a predetermined frequency, thereby removing a specific band from the input signal. The predetermined frequency, as used herein, refers to an upper limit of a frequency perceivable by the user as a tactile sense. For example, the predetermined frequency may be about 700 Hz. In addition, the predetermined frequency may be controlled depending on age of the user, gender, skin condition, and whether or not gloves are worn, etc. It is to be noted that the above-described predetermined frequency may be registered in advance in the storage section 180.

In addition, the band limit section 171 removes, from the vibration signal, a predetermined frequency component stored in advance, for example. More specifically, the storage section 180 stores a frequency corresponding to a predetermined frequency component in advance, and, in a case where a frequency component corresponding to the frequency is inputted, the band limit section 171 removes the frequency component from the input signal. Then, the band limit section 171 outputs, to the DRI 172 and the noise estimation section 175, the input signal with a specific band being removed.

The band limit section 171 removes a specific band in this manner, thereby preventing a vibration in a frequency region not corresponding to the tactile sense or a vibration of which a frequency is known in advance from being outputted from the vibration unit 120 provided in the master apparatus 10.

It is to be noted that the filter used by the band limit section 171 is not limited to the HPF or the LPF, and may be any filter. In addition, the method by which the band limit section 171 removes a specific band is not limited to the method using the filter, and may be any method.

DRI 172

The DRI 172 is a drive circuit, and has a function of driving the vibration unit 120 of the master apparatus 10 on the basis of an input signal. For example, the DRI 172 vibrates the vibration unit 120 on the basis of a vibration signal after removal of a specific band inputted from the band limit section 171. This causes the vibration unit 120 to generate a vibration corresponding to a tactile sense detected by the slave apparatus 50, thus transmitting to the user a tactile vibration generated at the surgical instrument.

A/D 173

The A/D 173 is an analog-to-digital conversion circuit (A/D conversion circuit), and has a function of converting an analog signal into a digital signal. For example, the A/D 173 receives an input signal from the force sensor 152 of the sensor unit 150, converts the input signal from an analog signal to a digital signal, and outputs the converted vibration signal to the adder 178. It is to be noted that the A/D 173 receives, as an input signal, external force including force of the user, gravity, inertia force, and a noise (hereinafter, also referred to as force+gravity+inertia force+noise) from the force sensor 152.

Inverse Dynamics Computation Section 174

The inverse dynamics computation section 174 has a function of performing inverse dynamics computation on action information on the master apparatus 10. The action information, as used herein, refers to measurement results of the motion sensor provided in the master apparatus 10. For example, the inverse dynamics computation section 174 corrects the force measured by the force sensor 152 by inverse dynamics computation. As described above, the force measured by the force sensor 152 is external force that includes at least one of gravity, inertia force, or a noise, in addition to the force of the user. Accordingly, it is difficult to maintain that the force measured by the force sensor 152 indicates accurate force of the user. Therefore, the inverse dynamics computation section 174 is able to determine the gravity and the inertia force by the inverse dynamics computation, and thus is able to calculate more accurate force of the user from the force measured by the force sensor 152.

Description is now given of the inverse dynamics computation. The inverse dynamics computation section 174 performs inverse dynamics computation on (θ, θ', and θ''), which are measurement results (i.e., action information) of the motion sensor provided in the master apparatus 10. Here, the (θ, θ', and θ'') represents (an angle of a joint, an angular velocity of a joint, and an angular acceleration of a joint). Typically, dynamics of a robot such as the master apparatus 10 of an embodiment of the present disclosure is represented by the following Mathematical Expression 1.

$$\tau = J(\theta)\theta'' + c(\theta,\theta') + g(\theta) \qquad \text{(Mathematical Expression 1)}$$

Here, left side of the above Mathematical Expression 1 indicates a torque value of each joint in the robot. In addition, the first, second, and third terms on right side of the above Mathematical Expression 1 indicate an inertial term, a centrifugal force and Coriolis force term, and a gravity term, respectively.

The inverse dynamics computation section 174 calculates gravity and inertia force applied to a force sensor part by providing a virtual joint in the force sensor part by means of a method utilizing the inverse dynamics computation, and subtracts the calculated gravity and inertia force from the external force to thereby calculate the more accurate force of the user.

It is to be noted that, in the embodiment of the present disclosure, the inverse dynamics computation section 174 calculates gravity generated by the self-weight of the operation apparatus 100 by the inverse dynamics computation, and outputs the gravity to the adder 178 as a minus value. In addition, the inverse dynamics computation section 174 calculates inertia force generated by the movement of the operation apparatus 100, and outputs the inertia force to the adder 178 as a minus value.

Noise Estimation Section 175

The noise estimation section 175 has a function of estimating a noise on the basis of an input signal. For example, the noise estimation section 175 estimates a noise caused by the vibration of the vibration unit 120 included in the external force measured by the force sensor 152 on the basis of the vibration signal after the removal of a specific band inputted from the band limit section 171.

The noise estimation section 175 may estimate a noise on the basis of a transfer function $H(\omega)$ estimated in advance. For example, a noise estimation section 175-1 illustrated in FIG. 5 determines the transfer function $H(\omega)$ of the operation apparatus 100 in advance by means of system identification. Then, the noise estimation section 175-1 estimates the noise caused by the vibration of the vibration unit 120 included in the external force measured by the force sensor 152 on the basis of the transfer function $H(\omega)$ and the vibration signal inputted from the band limit section 171. The transfer function (H), as used herein, refers to a function indicating a relationship between an input and an output.

In addition, the noise estimation section 175 may estimate the noise included in the external force by using an adaptive filter for the vibration signal inputted from the band limit section 171. Description is now given of the noise estimation in a case where the noise estimation section 175 uses the adaptive filter, with reference to FIG. 6. FIG. 6 illustrates an example of a noise estimation section 175-2 in which the signal processor 170 uses an ADF (Adaptive Digital Filter: adaptive filter) as the noise estimation section 175. In addition, it is assumed that the signal processor 170 illustrated in FIG. 6 uses, as the ADF of the noise estimation section 175-2, an FIR (Finite Impulse Response) filter which is a feedback circuit. Here, the adaptive filter is a filter that self-adapts the transfer function (H).

The noise estimation section 175-2 outputs a noise estimated on the basis of the vibration signal inputted from the band limit section 171 to the adder 179. The adder 179 to which the noise is inputted performs addition using a result of the addition of the adder 178 and the noise, and outputs the result of the addition. Then, an error signal corresponding to the result of the addition is fed back to the noise estimation section 175-2 by the feedback circuit, and the ADF of the noise estimation section 175-2 is able to adjust the transfer function (H) to reduce the error on the basis of the feedback.

Then, the noise estimation section 175 outputs the noise estimated by any of the above-described methods to the adder 179 as a minus value.

Adder 178 and Adder 179

The adder 178 and the adder 179 are each an arithmetic unit that performs addition. For example, the adder 178 and the adder 179 perform addition on the basis of a plurality of inputted values. Specifically, the adder 178 adds, to the external force (force+gravity+inertia force+noise) inputted from the A/D 173, the gravity and the inertia force inputted from the inverse dynamics computation section 174 as minus values. Then, the adder 178 outputs the external force (force+noise) calculated by the addition to the adder 179.

In addition, the adder 179 adds, to the external force (force+noise) inputted from the adder 178, the noise inputted as a minus value from the noise estimation section 175. Then, the control unit 160 outputs, to the high-level control section 190, the external force (force) calculated by the addition by the adder 179, as a signal (second signal).

(Storage Section 180)

The storage section 180 is a device for storing information regarding the master apparatus 10. For example, the storage section 180 stores data to be outputted in processing of the signal processor 170 and data of various applications and the like.

(High-Level Control Section 190)

The high-level control section 190 has a function related to control of the operations of the slave apparatus 50. For example, the high-level control section 190 receives the vibration signal measured by the sensor of the slave apparatus 50 from the slave apparatus 50, and outputs the drive signal to the band limit section 171 of the signal processor 170. In addition, the high-level control section 190 receives input of a signal calculated by the signal processor 170 on the basis of the drive signal from the adder 179 of the signal processor 170 to drive the slave apparatus 50 in response to the signal.

The description has been given above of the internal configuration example of the master apparatus 10 according to an embodiment of the present disclosure with reference to FIGS. 3 to 6.

The description has been given above of the master apparatus 10 of an embodiment of the present disclosure with reference to FIGS. 2 to 6. Next, description is given of a first embodiment.

3. FIRST EMBODIMENT

In the first embodiment, description is given of an example in which a stylus-type grasping interface is used as the operation apparatus 100 which is a tactile presentation apparatus according to the first embodiment.

3.1. External Configuration Example of Operation Apparatus

Hereinafter, description is given of an external configuration example of the operation apparatus 100 according to the first embodiment of the present disclosure, with reference to FIGS. 7 to 15.

<3.1.1. Overall Configuration Example>

Figure 7:
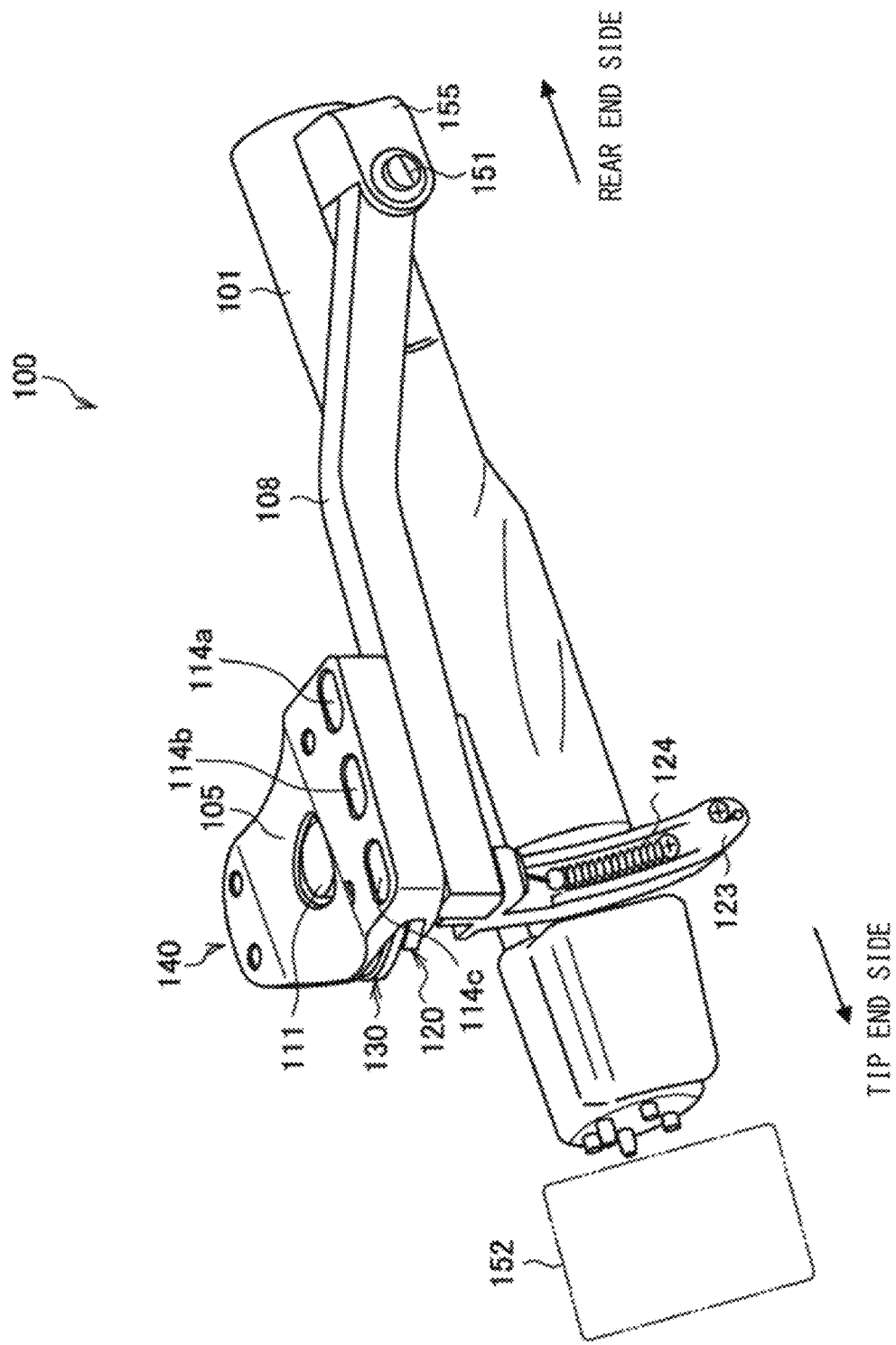
FIG. 7 is a perspective view of a tactile presentation apparatus according to a first embodiment of the present disclosure.
Figure 8:
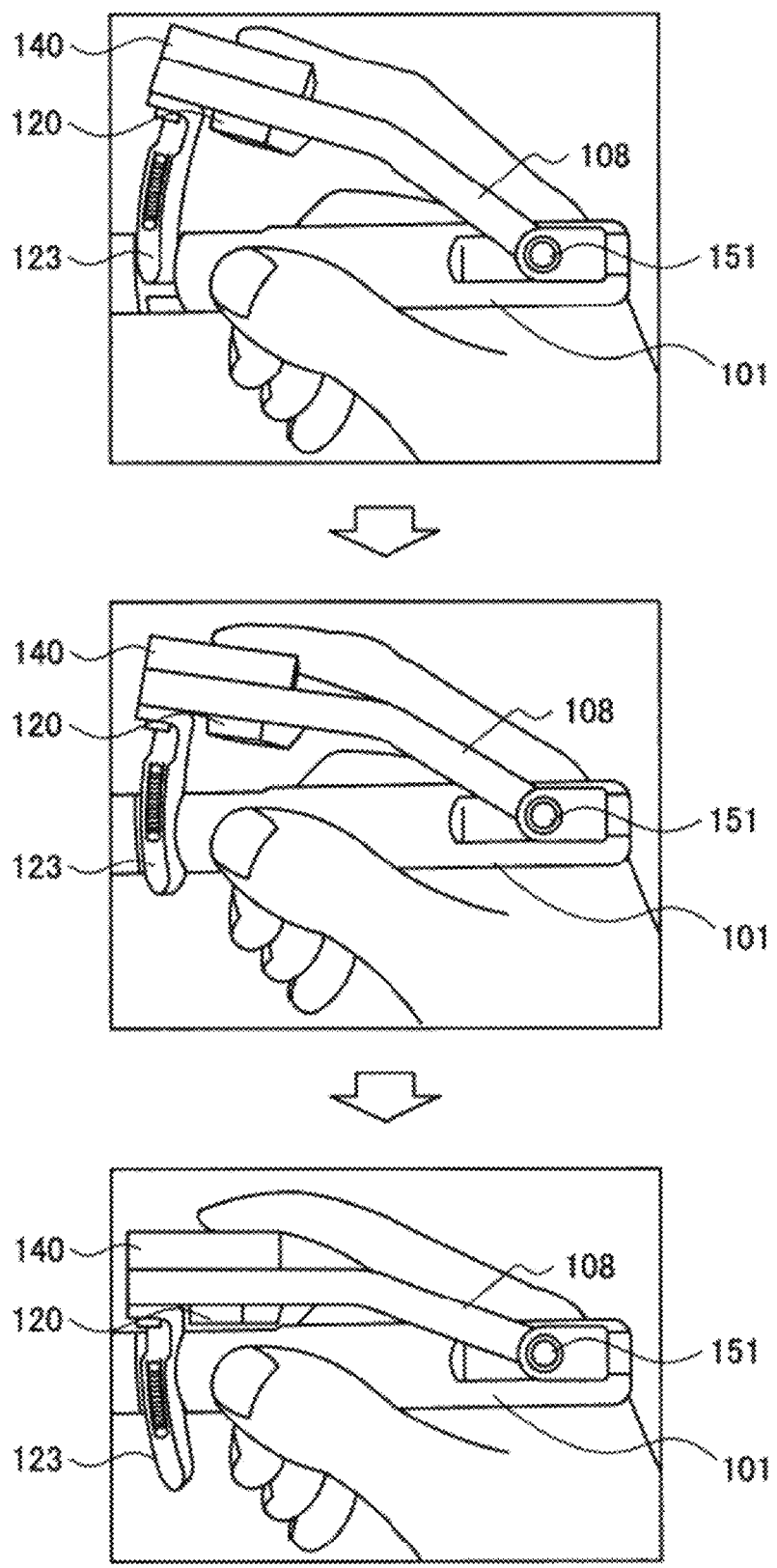
FIG. 8 is an explanatory diagram illustrating an operation example of the tactile presentation apparatus according to the same embodiment.

First, description is given of an overall configuration example of the operation apparatus 100 according to the first embodiment of the present disclosure, with reference to FIGS. 7 and 8. FIG. 7 is a perspective view of the tactile presentation apparatus according to the first embodiment of the present disclosure. FIG. 8 is an explanatory diagram illustrating an operation example of the tactile presentation apparatus according to the first embodiment of the present disclosure.

The operation apparatus 100 illustrated in FIG. 7 includes a housing 101 that accommodates therein a motor and an encoder. The housing 101 has an elongated rod-like outer shape as a whole for easy grasping by a user. That is, the operation apparatus 100 is a so-called stylus-type grasping interface. Such an operation apparatus 100 is attached to the fourth arm part 40*d* of the master apparatus 10 at tip end side thereof. The coupling part between the tip end side of the operation apparatus 100 and the fourth arm part 40*d* is provided with the force sensor 152.

A rotational axis member 151 is provided on rear end side of the housing 101. Both ends of the rotational axis member 151 are supported by a bearing part 155 and the housing 101. A master frame 108 as a frame part is pivotally linked to the rotational axis member 151 about the rotational axis member 151.

The master frame 108 is an elongated member disposed on one side surface side of the operation apparatus 100 along a longitudinal direction of the operation apparatus 100, and extends along a direction across an axial direction of the rotational axis member 151. An installation unit 140, which has a surface intersecting the rotational direction of the master frame 108 and extending along the longitudinal direction of the operation apparatus 100, is provided at an appropriate position on the tip end side of the master frame 108. The installation unit 140 is attached to the master frame 108 via holes 114 (holes 114*a*, 114*b*, and 114*c*) using a fixing means such as a screw or a bolt.

A surface on front side of the installation unit 140 constitutes a second contact surface 105 with which a finger of the user comes into contact. The second contact surface 105 has an arcuate concave shape to facilitate adaptation to a shape of the finger of the user. As illustrated in FIG. 8, the user grasps the operation apparatus 100 as if gripping a writing pen; at this time, for example, pressing the index finger against the second contact surface 105 enables the master frame 108 to pivot. It is to be noted that a surface on which the second contact surface 105 is provided is also considered as a surface, of the installation unit 140, in a direction opposite to the pressing direction.

In addition, the vibration unit 120 is provided in the vicinity of the installation unit 140. Specifically, the vibration unit 120 is provided on back side of the installation unit 140 with a contact unit 130 interposed therebetween. In addition, the contact unit 130 has a first contact surface 111 with which the finger of the user comes into contact. Therefore, upon vibration of the vibration unit 120 when the finger of the user is in contact with the first contact surface, the vibration of the vibration unit 120 is transmitted to the finger of the user via the first contact surface 111. It is to be noted that the first contact surface 111 comes into contact with a site, of the finger of the user in contact with the second contact surface 105, that is not in contact with the second contact surface 105. Typically, the ball of the index finger comes into contact with the first contact surface 111, and a site other than the ball of the index finger comes into contact with the second contact surface 105. Thus, the contact unit 130 transmits the vibration generated by the vibration unit 120 to the site of the finger of the user that is partially in contact with the first contact surface 111.

The vibration unit 120 generates a vibration corresponding to a tactile vibration acting on the surgical instrument of the slave apparatus 50 as described above, and the vibration is presented to the user via the first contact surface 111 of the contact unit 130.

In addition, the tip end side of the master frame 108 is provided with a rail unit 123 extending in a rotational direction of the master frame 108. The rail unit 123 has a substantially arcuate outer shape, and pivots along the extending direction of the rail unit 123 along with the pivoting of the master frame 108. That is, the rail unit 123 rotates about the rotational axis member 151.

In addition, a wire disposed on the rail unit 123 serves as a power transmission member, and drive torque generated by the motor is transmitted via the wire to the rail unit 123. Meanwhile, rotational torque of the rail unit 123 may also be transmitted via the wire to the motor along with the pivoting of the rail unit 123.

In addition, the end of the wire is fixed to one end of a spring 124 fixed to the rail unit 123 through a hole provided in the rail unit 123. This imparts tension to the wire through utilization of elastic force of the spring 124, thus making it possible to suppress the slack of the wire on the rail unit 123. The spring 124 is an example of a configuration for imparting tension to the wire; another tension generation part may be employed.

As described above, the coupling part between the operation apparatus 100 and the fourth arm part 40*d* of the support arm part 40 is provided with the force sensor 152. The force sensor 152 may be a six-axis force sensor that detects force and torsion of three-directional and six-axis components to be inputted to the operation apparatus 100 operated by the user. In a case where a translational force or torsional force is applied to the operation apparatus 100, the force sensor 152 generates an output corresponding to moment of the force. In a case of applying force control to the position and the orientation of the surgical instrument of the slave apparatus 50, the above-described control unit 160 detects force moment inputted to the operation apparatus 100 using the force sensor 152, and controls the posture of the arm of the slave apparatus 50 on the basis of the force moment. This makes it possible to smoothly control the position and the orientation of the surgical instrument attached to the slave apparatus 50.

In such an operation apparatus 100, the motor and the encoder are each electrically coupled to the above-described control unit 160 by an unillustrated cable or the like. The force sensor 152, which detects the force to be inputted to the operation apparatus 100, is also electrically coupled to the control unit 160. In addition, the vibration unit 120 is also electrically coupled to the control unit 160. Thus, the detection signals of the encoder and the force sensor 152 are outputted to the control unit 160, and a drive signal is inputted from the control unit 160 to the motor. In addition, the drive signal is inputted from the drive circuit of the control unit 160 to the vibration unit 120.

It is to be noted that the cable or the like described above may be wired inside the operation apparatus 100 or may be wired outside the operation apparatus 100.

The description has been given above, with reference to FIGS. 7 and 8, of the overall configuration example of the operation apparatus 100 according to the first embodiment of the present disclosure. Subsequently, description is given of a floating structure according to the first embodiment of the present disclosure.

<3.1.2. Configuration Example of Floating Structure Part>

Figure 9:
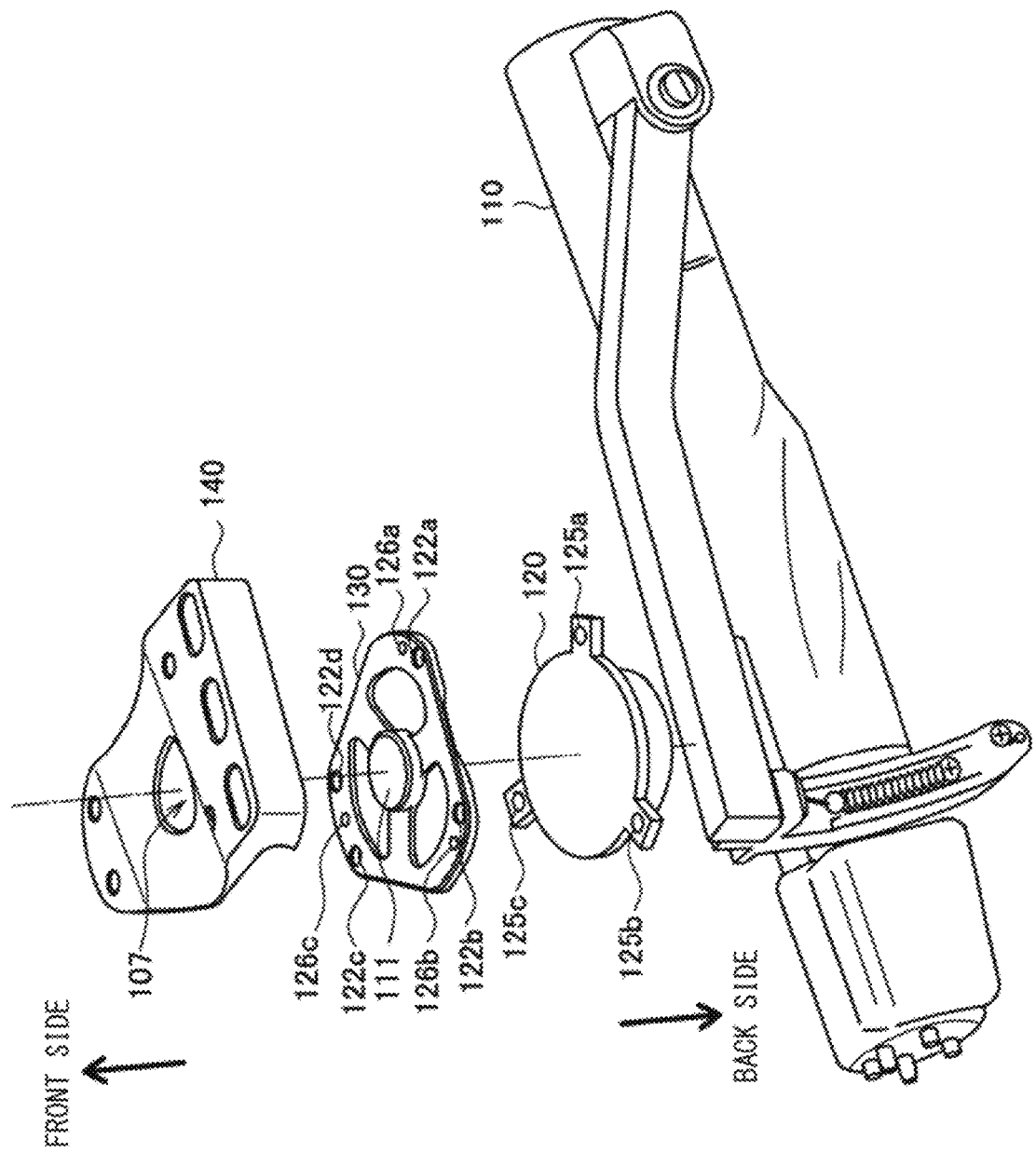
FIG. 9 is an explanatory diagram illustrating a partial configuration example of the tactile presentation apparatus according to the same embodiment.
Figure 10:
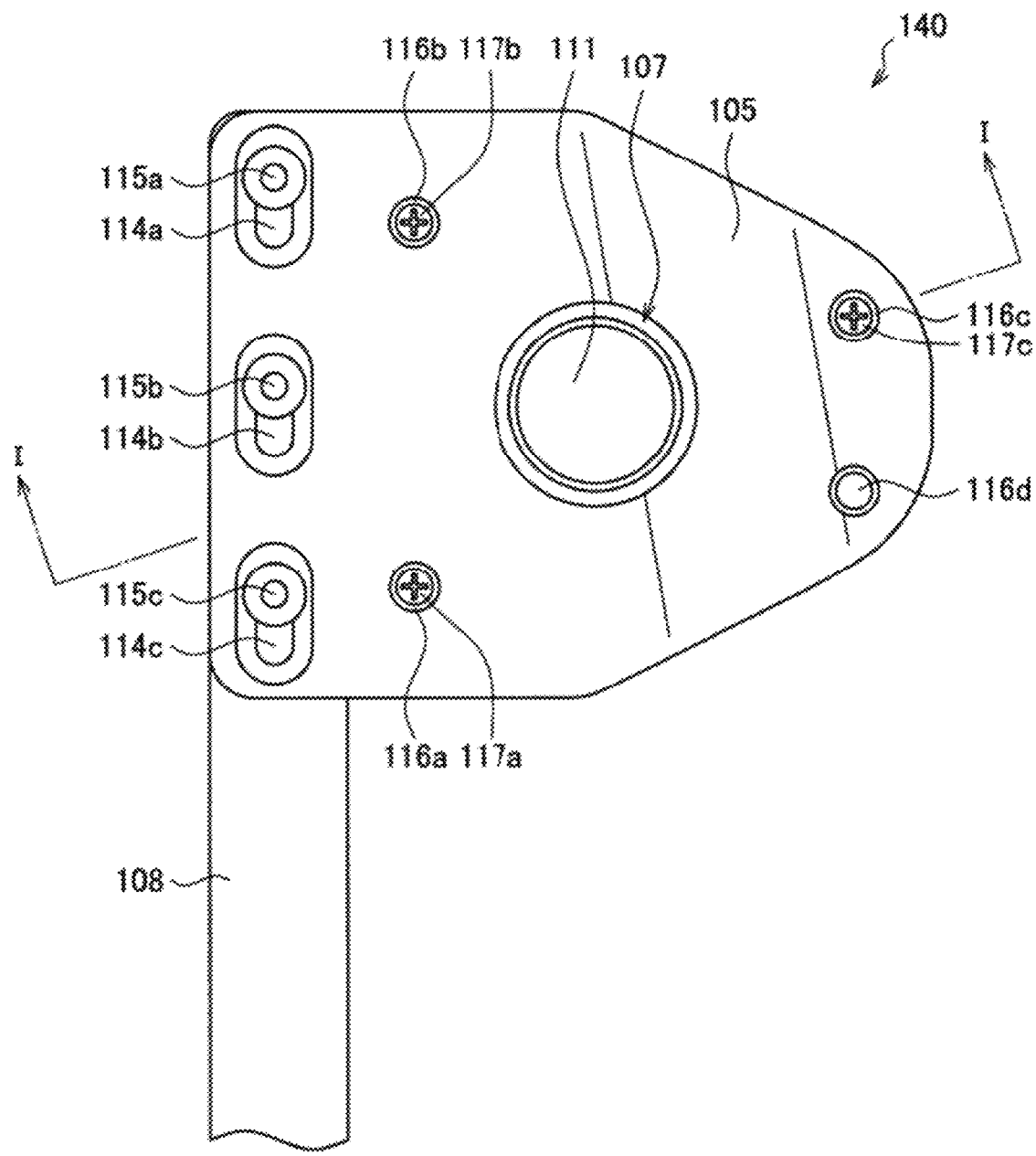
FIG. 10 is an explanatory diagram illustrating an example of assembling the tactile presentation apparatus according to the same embodiment.
Figure 11:
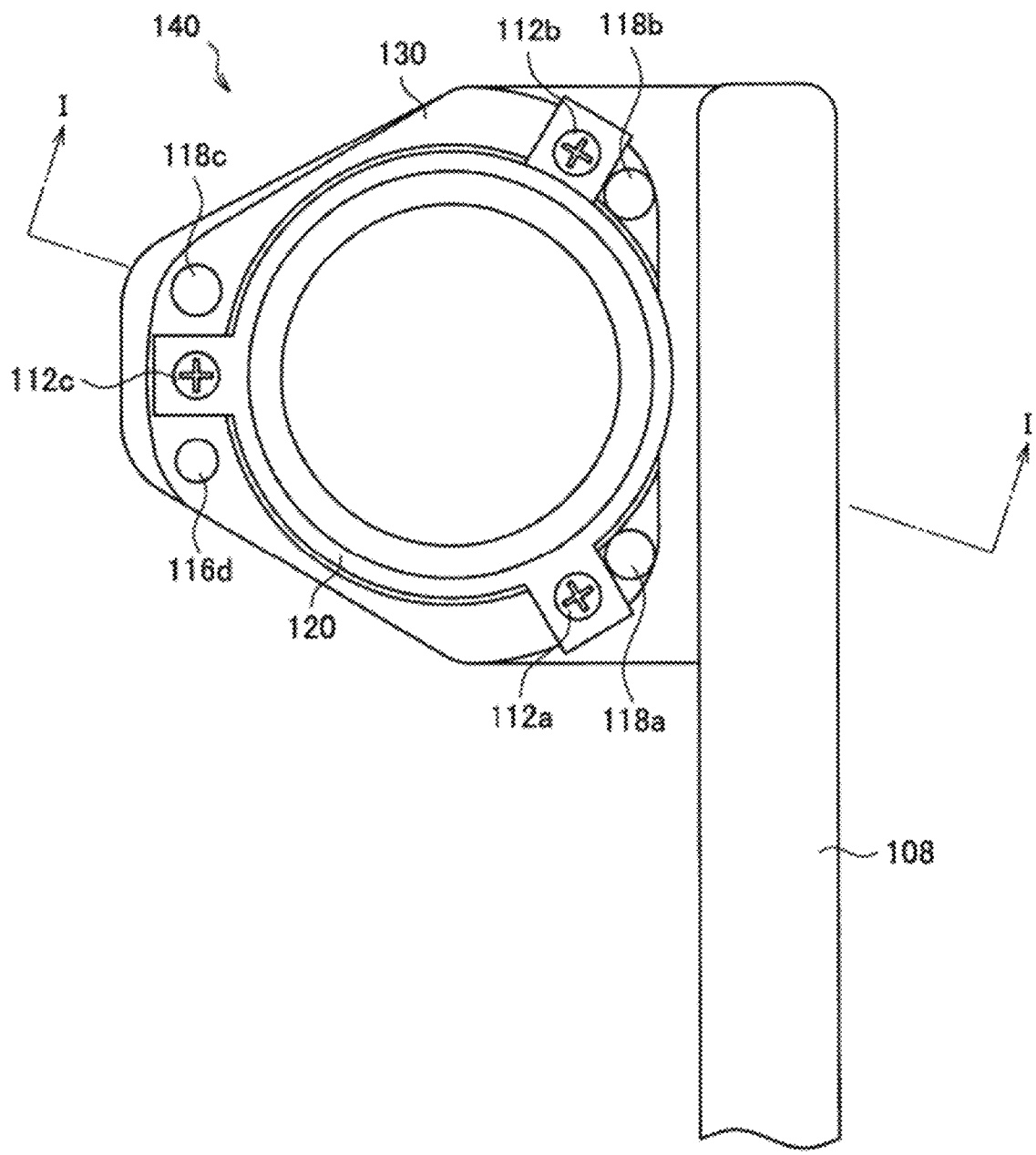
FIG. 11 is an explanatory diagram illustrating an example of assembling the tactile presentation apparatus according to the same embodiment.
Figure 12:
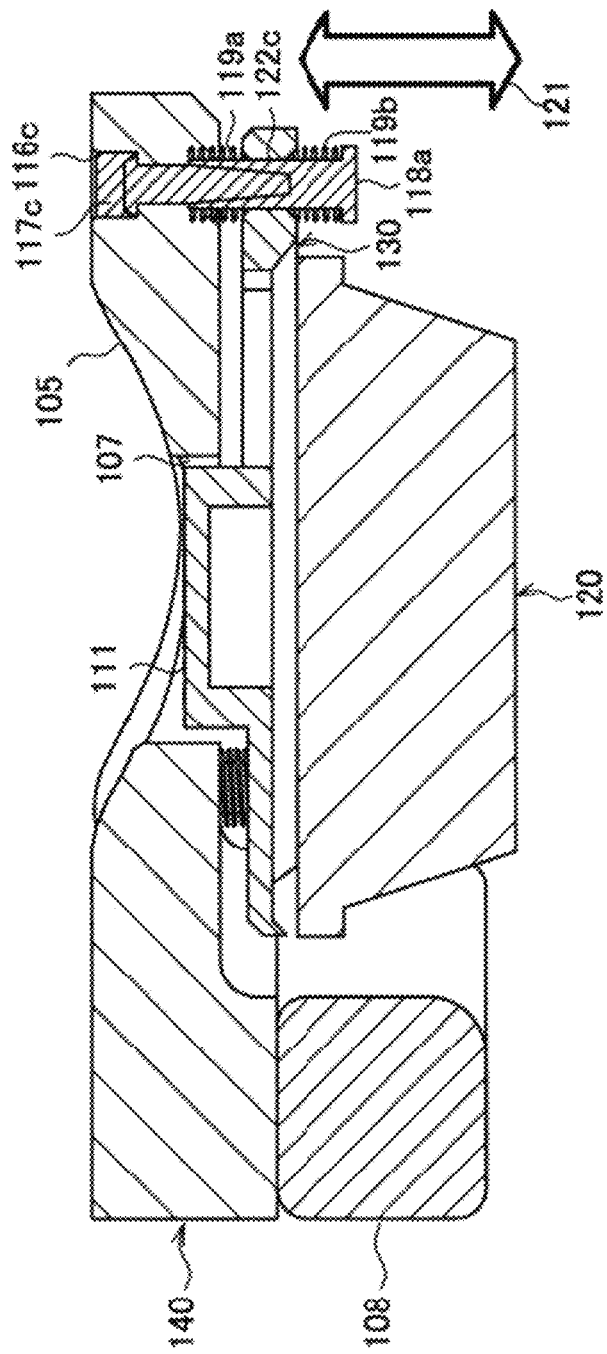
FIG. 12 is a cross-sectional view of a floating structure part of the tactile presentation apparatus according to the same embodiment.

Hereinafter, description is given of a configuration example of a floating structure part of the tactile presentation apparatus according to the first embodiment of the present disclosure, with reference to FIGS. 9 to 13. FIG. 9 is an explanatory diagram illustrating a partial configuration example of the tactile presentation apparatus according to the first embodiment of the present disclosure. FIG. 10 is an explanatory diagram illustrating an example of assembling the tactile presentation apparatus according to the first embodiment of the present disclosure as viewed from the front side of the installation unit 140. FIG. 11 is an explanatory diagram illustrating an example of assembling the tactile presentation apparatus according to the first embodiment of the present disclosure as viewed from the back side of the installation unit 140. FIG. 12 is a cross-sectional view of the floating structure part along a cutting line I of the tactile presentation apparatus according to the first embodiment of the present disclosure. The front side, as used in this section, refers to side in a direction opposite to the pressing direction of the master frame 108. In addition, the back side refers to side in the pressing direction of the master frame 108.

As illustrated in FIG. 9, the operation apparatus 100 according to the first embodiment of the present disclosure is roughly configured by four units. Specifically, the operation apparatus 100 is configured by an operation unit 110, the vibration unit 120, the contact unit 130, and the installation unit 140. The floating structure part according to the first embodiment of the present disclosure is configured by the vibration unit 120, the contact unit 130, and the installation unit 140. The floating structure according to the first embodiment of the present disclosure is a structure for suppressing transmission of the vibration generated by the vibration unit 120 to the force sensor 152.

The operation unit 110 is a unit to be operated by the user in the operation apparatus 100. It is to be noted that the above-described housing 101 and the master frame 108 that pivots about the rotational axis member 151 correspond to the operation unit according to the first embodiment of the present disclosure. In addition, as illustrated in FIG. 7, the force sensor 152 is coupled to tip end side of the housing 101 of the operation unit 110. The user grasps and operates the operation unit 110 to thereby cause the force sensor 152 to measure the force of the user to be inputted to the operation unit 110.

The installation unit 140 is a unit with which the finger of the user comes into contact. The installation unit 140 is attached to the master frame 108 by bolts 115 (bolts 115a, 115b, and 115c) through respective holes of the holes 114 (holes 114a, 114b, and 114c) illustrated in FIG. 10. As described above, the installation unit 140 has the second contact surface 105 with which the finger of the user comes into contact. In addition, as illustrated in FIG. 9, the installation unit 140 has the second contact surface 105 with which the finger of the user comes into contact, and an opening 107 that penetrates between side of the second contact surface 105 and back side of the second contact surface.

It is to be noted that the shape of the opening 107 is not limited to the circular shape illustrated in FIG. 9. For example, the shape of the opening 107 may be a polygonal shape such as a square. In addition, the opening 107 may be located not only in the vicinity of the middle of the installation unit 140 as illustrated in FIG. 9, but may also be the opening 107 that reaches an outer periphery from the vicinity of the middle of the installation unit 140.

The contact unit 130 is a unit that transmits the vibration generated by the vibration unit 120 to the user. The contact unit 130 has the first contact surface 111 to be in contact with the finger of the user. The contact unit 130 is able to transmit the vibration directly to the finger of the user by the first contact surface 111. As illustrated in FIG. 12, a protruded part of the contact unit 130 is inserted from back side of the second contact surface 105 into the opening 107 provided in the installation unit 140. A surface, of such a protruded part, of a part that comes into contact with the finger of the user on the front side of the installation unit 140 (i.e., side on which the second contact surface 105 is provided) constitutes the first contact surface 111. Such a configuration allows both of the first contact surface 111 and the second contact surface 105 to come into contact with the same finger of the user. Accordingly, when the user performs an operation of pivoting the master frame 108 by pressing the second contact surface 105 with a finger, the vibration generated by the vibration unit 120 is transmitted to the finger that has pressed the second contact surface 105. This makes it possible to achieve a feedback equivalent to a tactile sense transmitted to a finger operating forceps when an object is gripped by the forceps, for example.

The contact unit 130 is slidably disposed on the back side of the installation unit 140. Specifically, columnar fixtures 118 (fixtures 118a, 118b, and 118c) having cross-sectional shapes smaller than those of holes 122 (holes 122a, 122b, and 122c) provided in the contact unit 130 are inserted into the holes 122 to allow the contact unit 130 to be slidably disposed along the fixtures 118. The fixtures 118 are fixed to the installation unit 140 by screws 117 (screws 117a, 117b, and 117c) inserted from holes 116 (holes 116a, 116b, and 116c) on the front side of the installation unit 140 illustrated in FIG. 10. Such a configuration makes it possible for the contact unit 130 to slide along the fixture 118 when vibrating together with the vibration unit 120.

Here, the contact unit 130 is attached to the installation unit 140 via an elastic body to have no direct contact with the installation unit 140. For example, as illustrated in FIG. 12, the contact unit 130 is attached to the installation unit 140 while being sandwiched by two springs 119 (springs 119a and 119b) which are elastic bodies, with respect to the hole 122c. More specifically, the spring 119a is mounted between front side, with the first contact surface 111, of the contact unit 130 and back side (a surface on side opposite to the second contact surface 105) of the installation unit 140. In addition, the spring 119b is mounted between back side (a surface on side opposite to the first contact surface 111) of the contact unit 130 and the head of the fixture 118b. The same applies to the unillustrated holes 122a and 122b. Such a configuration allows at least a portion of the vibration to be absorbed by the elastic body when the contact unit 130 and the vibration unit 120 vibrate together. Thus, it is possible to suppress the vibration transmitted from the contact unit 130 to the installation unit 140; as a result, it is also possible to suppress the vibration transmitted to the force sensor 152 via the operation unit 110 to which the installation unit 140 is attached.

It is to be noted that a lightweight component made of aluminum, magnesium, or the like is desirably used for the contact unit 130. The use of the lightweight component for the contact unit 130 reduces an influence of the self-weight of the contact unit 130 on a measured value of the force sensor 152, and further reduces mass thereof to be vibrated by the vibration unit 120, thereby making it possible to reduce the size of the actuator used as the vibration unit 120.

The fixture 118 is inserted into space inside the spring 119. This allows a direction in which the spring 119 expands and contracts and the sliding direction of the contact unit 130 to coincide with each other, thus making it possible to fix the sliding direction of the contact unit 130 to one axis. In addition, when the finger of the user touches the first contact surface 111, the contact unit 130 is slid to thereby enable its position to be changed so as to fit to the finger of the user.

It is to be noted that the number of elastic bodies is not limited to the number used in the above example, and any number of elastic bodies may be used. For example, although two springs 119 are used in the hole 122c described above, only one spring 119 may be used by coupling the installation unit 140 and the contact unit 130 directly with a spring. In a case where the same applies also to the unillustrated holes 122a and 122b, it follows that three springs 119 are used as a whole. In addition, one spring 119 may be used throughout the contact unit 130 and the installation unit 140, rather than one spring for each hole 122. In addition, elastic bodies are preferably arranged in a well-balanced manner around the protruded part of the contact unit 130 to come into contact with the contact unit 130. For example, two elastic bodies may be arranged one by one at positions opposed to each other with the protruded part of the contact unit 130 interposed therebetween. The elastic bodies arranged in a well-balanced manner allows the contact unit 130 to be installed stably without being inclined. Then, when the user presses the protruded part of the contact unit 130 in a direction of the back side of the installation unit 140, the contact unit 130 is able to be translated without being inclined.

In addition, the elastic body is not limited to the spring described above, and any elastic body may be used. For example, rubber, or a flexible material, etc. may be used as the elastic body.

It is to be noted that there are four holes 122, including the hole 122d, as the hole 122 used to attach the contact unit 130; however, it is sufficient to use at least two of the four holes 122. For example, it is sufficient to use two holes 122 opposed to each other with the protruded part of the contact unit 130 interposed therebetween. Specifically, it is sufficient to use two holes 122, i.e., a combination of the hole 122a and the hole 122c or a combination of the hole 122b and the hole 122d. The use of the two holes 122, among the four holes 122, opposed to each other with the protruded part of the contact unit 130 interposed therebetween in this manner allows the contact unit 130 to be stably installed.

As described above, the structure in which the contact unit 130 is attached to the installation unit 140 via the elastic body, with the contact unit 130 and the installation unit 140 being in non-contact is referred to as a floating structure. It is to be noted that the contact unit 130 attached to the installation unit 140 via the elastic body allows the contact unit 130 and the operation unit 110 to be in non-contact, thus causing the contact unit 130 and the operation unit 110 to be separated from each other.

The vibration unit 120 is provided on back side of the first contact surface of the contact unit 130. Specifically, screws 112 (screws 112a, 112b, and 112c) illustrated in FIG. 11 are penetrated into holes 125 (holes 125a, 125b, and 125c) of the vibration unit 120 illustrated in FIG. 9 from back side thereof. Then, the screws 112 are fixed to screw holes 126 (screw holes 126a, 126b, and 126c) of the contact unit 130. In this manner, the vibration unit 120 is fixedly attached to the back side of the contact unit 130.

In addition, the vibration unit 120 vibrates in a direction corresponding to the direction in which the elastic body expands and contracts. For example, the vibration unit 120 vibrates in a direction coincident or substantially coincident with the direction in which the elastic body expands and contracts. Specifically, the vibration unit 120 vibrates in the direction of a vibration direction 121 illustrated in FIG. 12.

The vibration direction 121 coincides with directions in which the springs 119a and 119b, which are elastic bodies illustrated in FIG. 12, expand and contract. Typically, the elastic body exhibits higher vibration absorbing capacity as direction of the force applied to the elastic body more coincides with the direction of expansion and contraction. Accordingly, the vibration unit 120 vibrating in a direction coincident or substantially coincident with the direction in which the elastic body expands and contracts makes it possible for the elastic body to efficiently absorb the vibration generated by the vibration unit 120.

Figure 13:
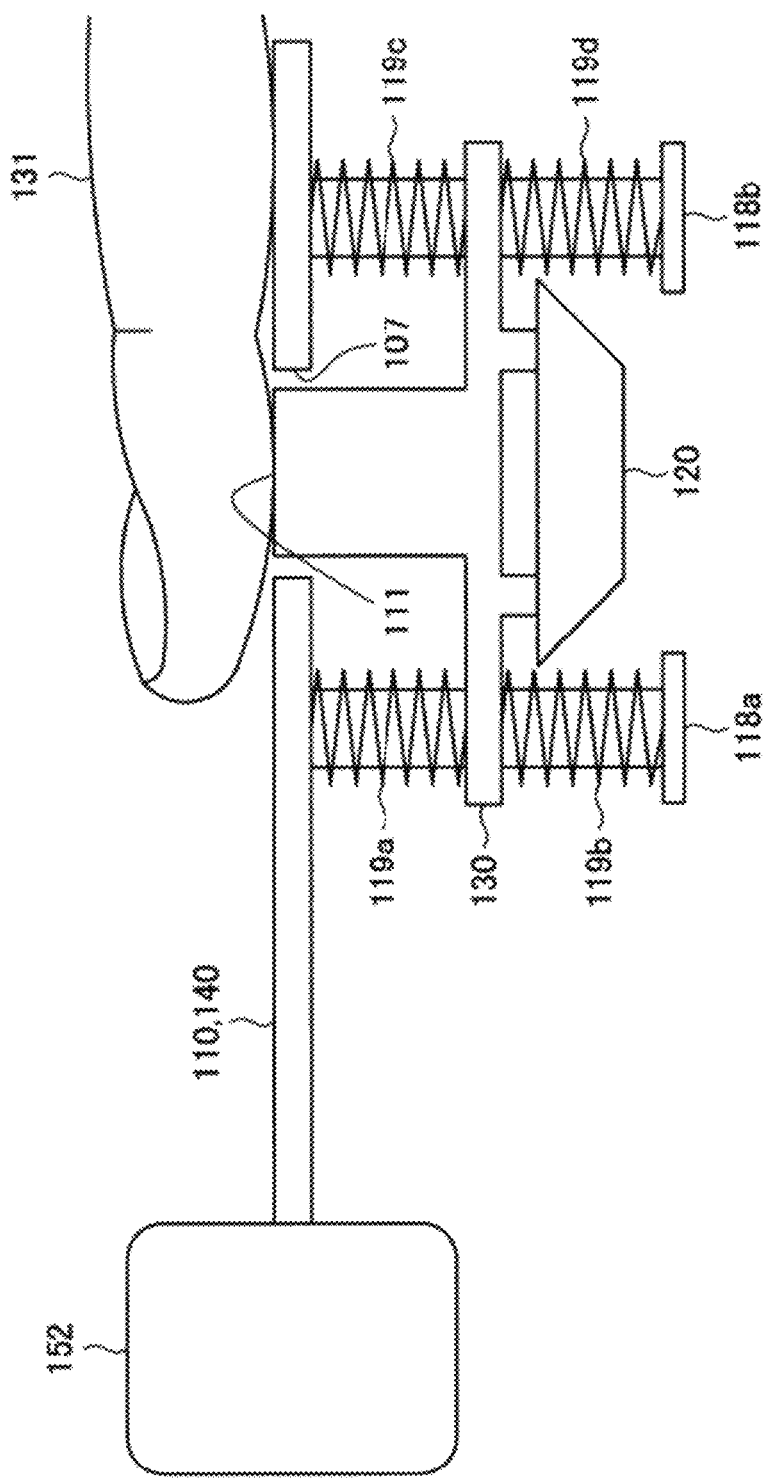
FIG. 13 is a simplified diagram illustrating the tactile presentation apparatus according to the same embodiment.

Here, the floating structure described above is summarized with reference to FIG. 13. FIG. 13 is a simplified diagram illustrating the tactile presentation apparatus according to the first embodiment of the present disclosure. It is to be noted that FIG. 13 illustrates the operation unit 110 and the installation unit 140 collectively in one diagram. The contact unit 130 is provided with the vibration unit 120. The installation unit 140 is provided with the contact unit 130 via the elastic bodies (springs 119a to 119d). Then, the installation unit 140 is provided in the operation unit 110. Thus, when the vibration unit 120 vibrates, the vibration generated from the vibration unit 120 is transmitted to the contact unit 130, and the contact unit 130 also vibrates together. Further, in a case where a finger 131 of the user is in contact with the first contact surface 111 of the contact unit 130, the vibration generated from the contact unit 130 is transmitted to the finger of the user via the first contact surface 111.

In addition, the contact unit 130 is slidably disposed along the fixture 118 relative to the installation unit 140 by the fixtures 118 (fixtures 118a and 118b). In addition, the contact unit 130 is attached to the installation unit 140 while being sandwiched by the elastic bodies (springs 119a and 119b), with respect to the fixture 118a. In addition, the contact unit 130 is attached to the installation unit 140 while being sandwiched by the elastic bodies (springs 119c and 119d), with respect to the fixture 118b. Accordingly, when the contact unit 130 and the vibration unit 120 vibrate together, at least a portion of the vibration is absorbed by the elastic body. Thus, it is possible to suppress the vibration transmitted from the contact unit 130 to the installation unit 140; as a result, it is also possible to suppress the vibration transmitted to the force sensor 152 via the operation unit 110 to which the installation unit 140 is attached.

The description has been given above, with reference to FIGS. 9 to 13, of the configuration example of the floating structure part of the tactile presentation apparatus according to the first embodiment of the present disclosure. Subsequently, description is given of an initial position of the first contact surface according to the first embodiment of the present disclosure.

<3.1.3. Initial position of First Contact Surface>

Figure 14:
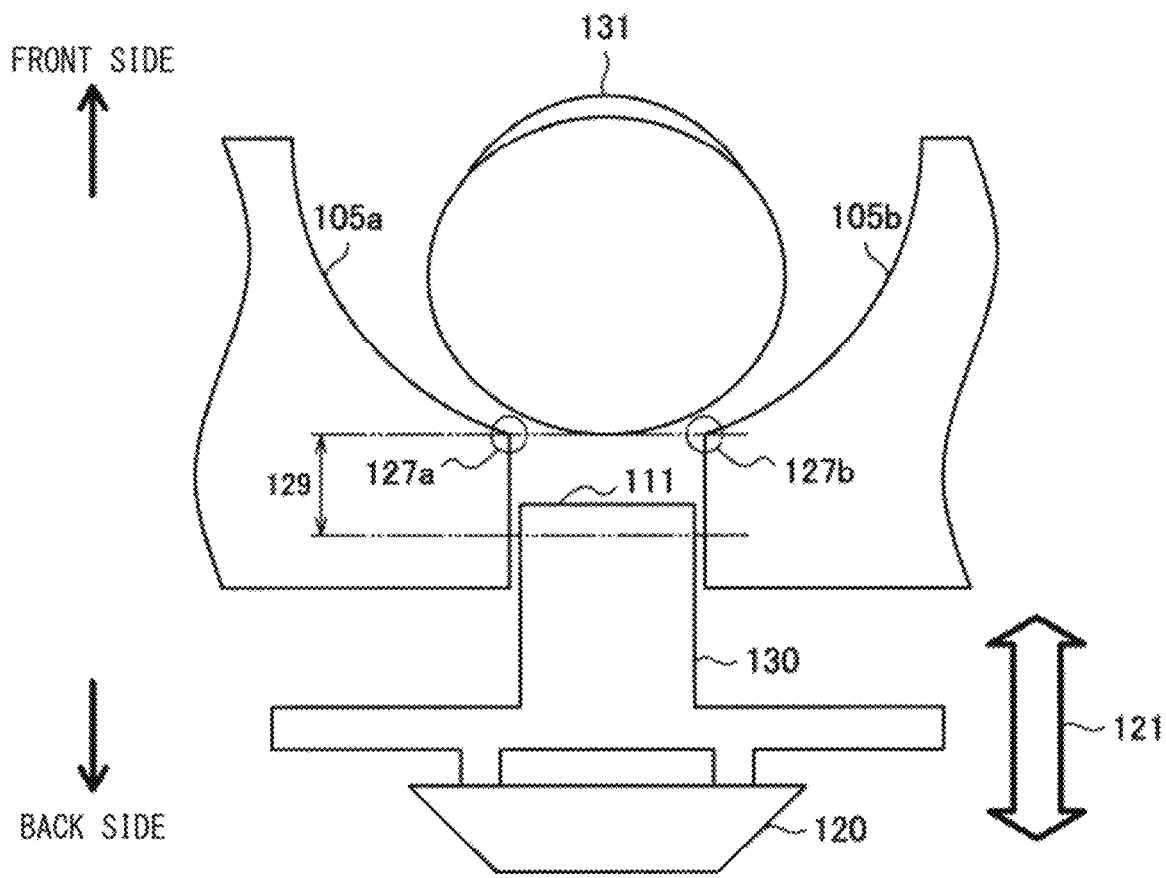
FIG. 14 is an explanatory diagram illustrating an example of an initial position of a first contact surface according to the same embodiment.
Figure 15:
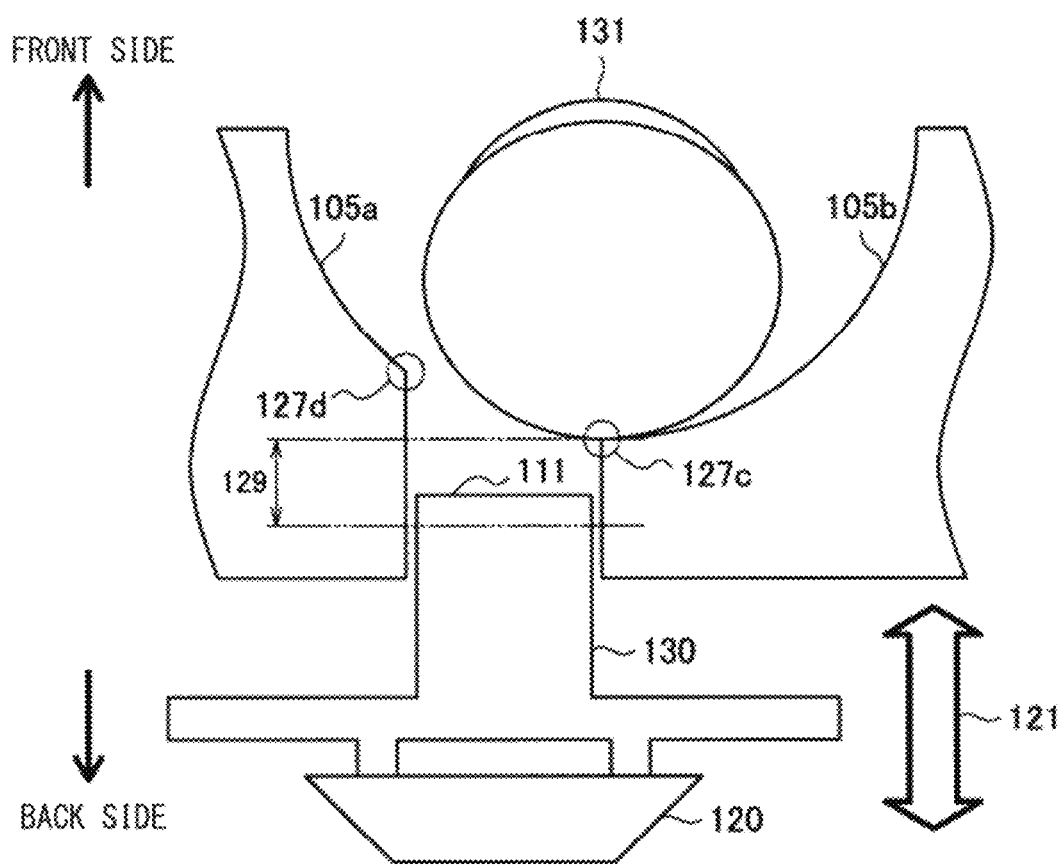
FIG. 15 is an explanatory diagram illustrating an example of the initial position of the first contact surface according to the same embodiment.

Hereinafter, description is given of an initial position of the first contact surface according to the first embodiment of the present disclosure, with reference to FIGS. 14 and 15. FIGS. 14 and 15 are each an explanatory diagram illustrating an example of the initial position of the first contact surface according to the first embodiment of the present disclosure.

In the above-described configuration, for example, in a case where the vibration unit 120 vibrates in the direction of the vibration direction 121 illustrated in FIG. 12, the contact unit 130 also vibrates in the direction of the vibration direction 121. At this time, there is a possibility, depending on magnitude of amplitude of the vibration unit 120 and the mounting position of the contact unit 130, that the first contact surface 111 of the contact unit 130 may not come into contact with the finger of the user. Therefore, in implementing the above-described configuration, the initial position of the first contact surface of the contact unit 130 is favorably set in consideration of the amplitude of the vibration unit 120. The initial position refers to a position of the first contact surface 111, with the vibration unit 120 being stopped (i.e., stationary). In other words, the initial position is the position of the first contact surface 111 at the time when the contact unit 130 is attached to the installation unit 140.

For example, the first contact surface 111 may favorably be at a position where the first contact surface 111 and the second contact surface 105 in the vibration direction of the vibration unit 120 are coincident or substantially coincident with each other, with the vibration unit 120 being stopped. The position coincident with the second contact surface 105 is, for example, a position coincident with an edge of the opening 107 on the front side (second contact surface side) of the installation unit 140 with respect to the vibration direction 121. The edge of the opening 107 is an end of the second contact surface 105 that forms the opening 107. More specifically, in the example illustrated in FIG. 14, the position coincident with the second contact surface 105 refers to a position coincident with an end 127a of a second contact surface 105a or an end 127b of a second contact surface 105b with respect to the vibration direction 121. In a case where the finger 131 of the user comes into contact with the second contact surface 105, the position of the ball of the finger 131 of the user is typically a position coincident with at least one of the ends 127 with respect to the vibration direction 121. Accordingly, when the initial position of the first contact surface 111 is a position coincident with at least one of the ends 127, the first contact surface 111 is able to come into contact with the finger 131 of the user upon the vibration of the vibration unit 120.

In addition, the position substantially coincident with the second contact surface 105 is a position where the shortest distance between the first contact surface 111 and the end 127 in the vibration direction is within a range of a value corresponding to the amplitude of the vibration unit 120. When considering the motion of the first contact surface 111 per cycle upon the vibration of the vibration unit 120, the first contact surface 111 first moves in a front-side direction of the installation unit 140 by the amplitude of the vibration unit 120 from the initial value. Next, the first contact surface 111 moves in a back-side direction of the installation unit 140 by twice the amplitude of the vibration unit 120. Finally, the first contact surface 111 moves in the front-side direction of the installation unit 140 by the amplitude of the vibration unit 120, and returns to the initial value. Accordingly, when the initial position of the first contact surface 111 is at a position within a distance 129 of the amplitude of the vibration unit 120 from the end 127 in the back-side direction of the installation unit 140, the first contact surface 111 is able to come into contact with the finger of the user upon the vibration of the vibration unit 120.

In addition, FIG. 14 illustrates an example in which the end 127a and the end 127b are positioned to be in coincident with each other with respect to the vibration direction 121; however, depending on the position of the opening 107, there may be a case where the position of the ends 127 are not coincident with respect to the vibration direction 121, as in an end 127c and an end 127d illustrated in FIG. 15. In this case, the initial position of the first contact surface 111 may favorably be set at a position coincident with the end 127c at which the distance from the first contact surface 111 is the shortest, or at a position within the distance 129 of the amplitude of the vibration unit 120 from the end 127c in the back-side direction of the installation unit 140.

The description has been given above, with reference to FIGS. 14 and 15, of the initial position of the first contact surface according to the first embodiment of the present disclosure. Consequently, description is given of an example of transmission of the vibration according to the first embodiment of the present disclosure.

The description has been given above, with reference to FIGS. 7 to 15, of the external configuration example of the operation apparatus 100 according to the first embodiment of the present disclosure. Consequently, description is given of an operation example according to the first embodiment of the present disclosure.

3.2. Operation Example

Figure 16:
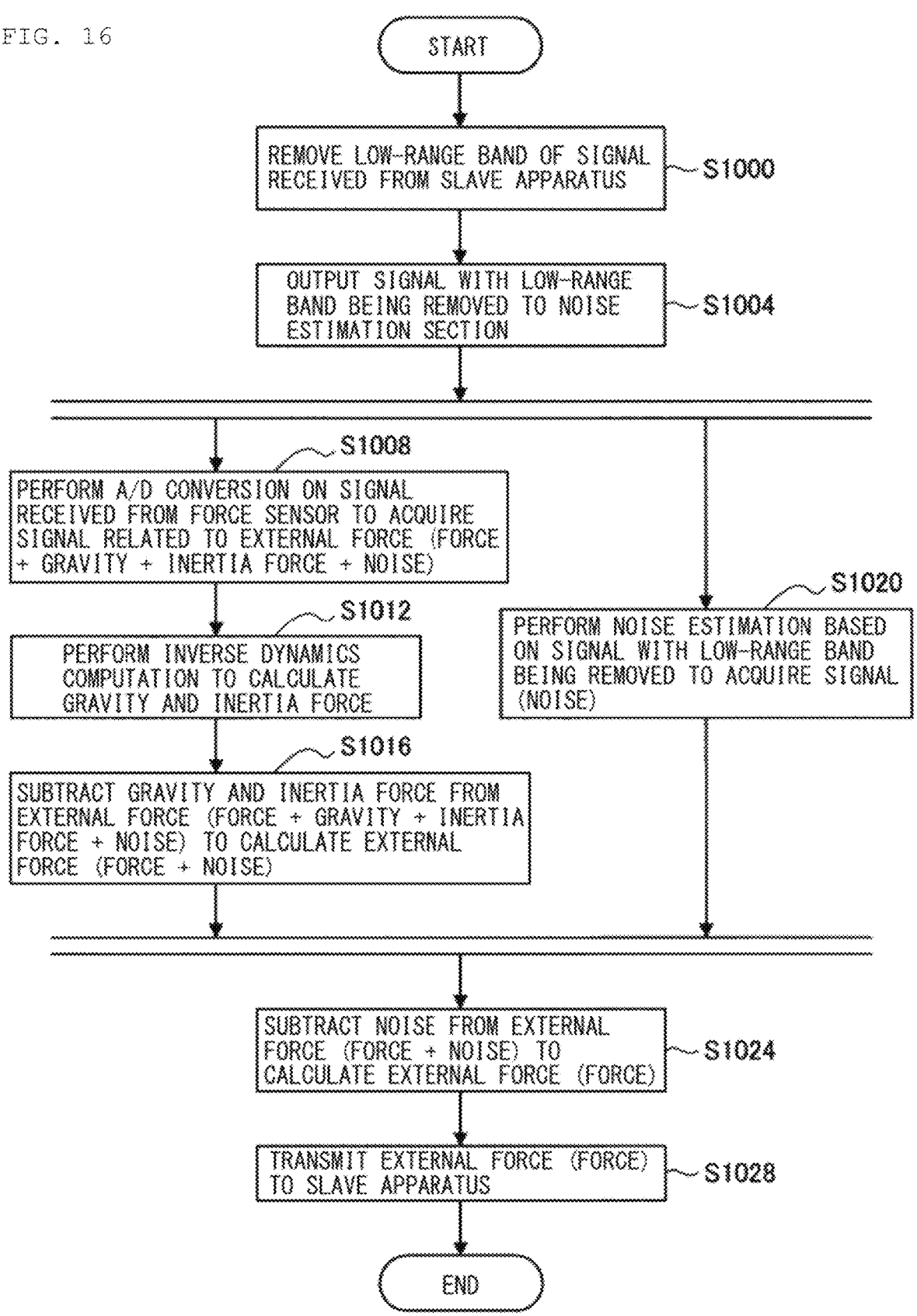
FIG. 16 is a flowchart illustrating an operation example of the signal processor according to the same embodiment.

Hereinafter, description is given of an operation example of processing of the signal processor 170 according to the first embodiment of the present disclosure with reference to FIG. 16. FIG. 16 is a flow chart illustrating an operation example of the signal processor according to the first embodiment of the present disclosure.

The signal processor 170 performs processing of removal of a specific band on an inputted signal. First, the signal processor 170 performs the processing of the removal of a specific band from a signal received by the high-level control section 190 from the slave apparatus 50. When a signal is inputted to the signal processor 170 from the high-level control section 190, the band limit section 171 of the signal processor 170 removes a low-range band from the signal using the HPF, for example (step S1000). The band limit section 171 outputs a signal after the removal of the low-range band to the noise estimation section 175 (step S1004).

In addition, the signal processor 170 performs noise reduction processing on a signal inputted from the force sensor 152. First, when a signal is inputted from the force sensor 152, the signal processor 170 performs conversion with the A/D 173, acquires a digital signal related to external force (force+gravity+inertia force+noise), and outputs the acquired digital signal to the adder 178 (step S1008). In addition, the inverse dynamics computation section 174 calculates, by inverse dynamics computation, gravity due to the self-weight of the operation apparatus 100 and inertia force generated by the movement of the operation apparatus 100, and outputs them as minus values to the adder 178 (step S1012). The adder 178 adds the minus values of gravity and inertia force to the external force (force+gravity+inertia force+noise) to thereby calculate external force (force+noise), and outputs the calculated external force to the adder 179 (step S1016).

In addition, in parallel with the above-described series of processing of steps S1008, S1012, and S1016, the noise estimation section 175 acquires a noise by noise estimation on the basis of the signal after the removal of the low-range band inputted from the band limit section 171, and outputs the noise as a minus value to the adder 179 (step S1020).

The adder 179 adds, to the external force (force+noise) inputted to the adder 178, the noise as a minus value inputted to the noise estimation section 175, and calculates external force (force) (step S1024). Then, the control unit 160 transmits a signal related to the external force (force) to the slave apparatus 50 (step S1028).

The description has been given above, with reference to FIG. 16, of the operation example in a case where the operation apparatus 100 according to the first embodiment of the present disclosure is applied to the master apparatus 10. Consequently, description is given of modification examples according to the first embodiment of the present disclosure.

3.3. Modification Examples

Hereinafter, description is given of modification examples according to the first embodiment of the present disclosure with reference to FIGS. 17 to 20. It is to be noted that the modification examples described below may be applied alone to the first embodiment of the present disclosure or may be applied in combination to the first embodiment of the present disclosure. In addition, the modification example may be applied in place of the configuration described in the first embodiment of the present disclosure, or may be applied additionally to the configuration described in the first embodiment of the present disclosure.

(1) First Modification Example

Figure 17:
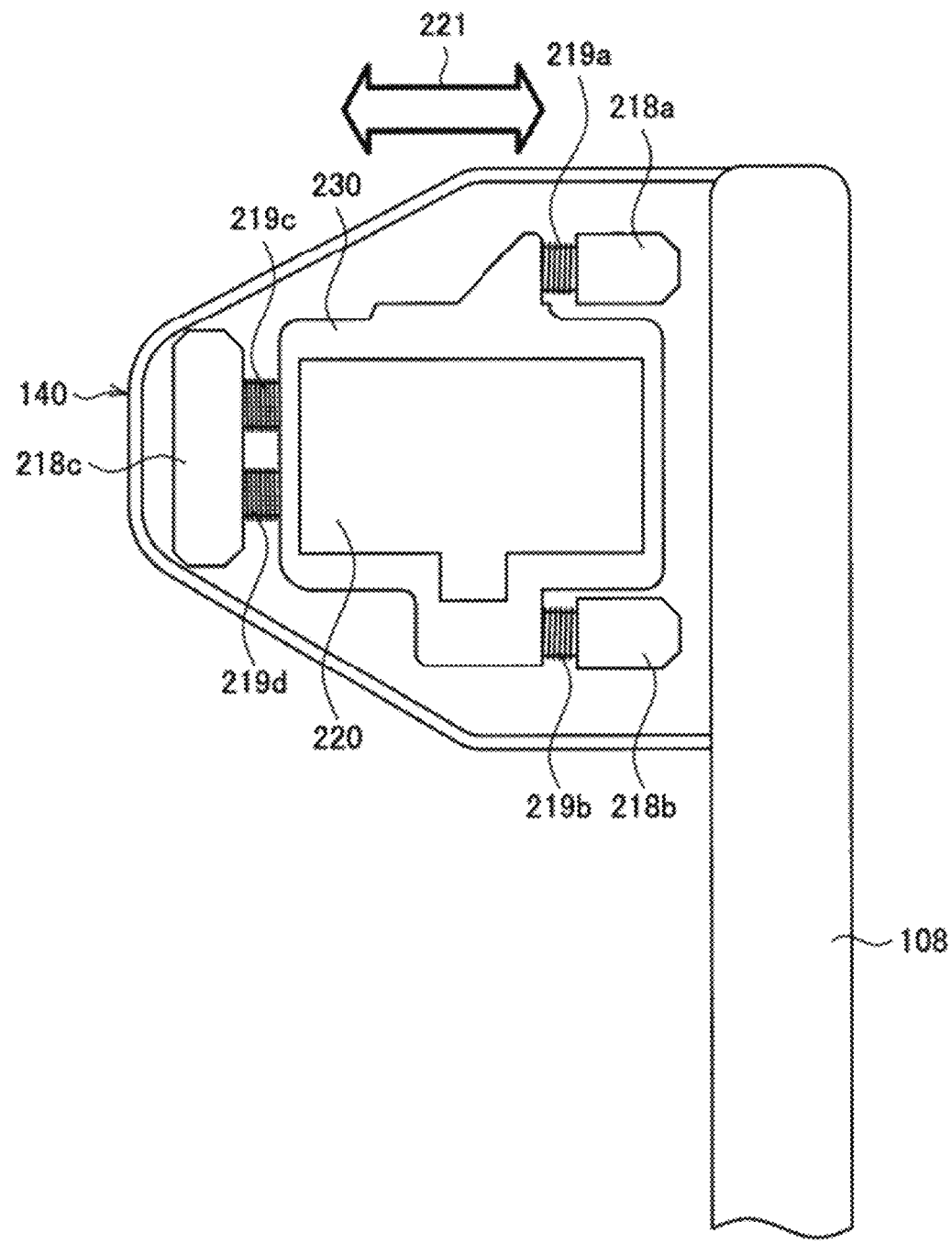
FIG. 17 is an explanatory diagram illustrating a first modification example according to the same embodiment.
Figure 18:
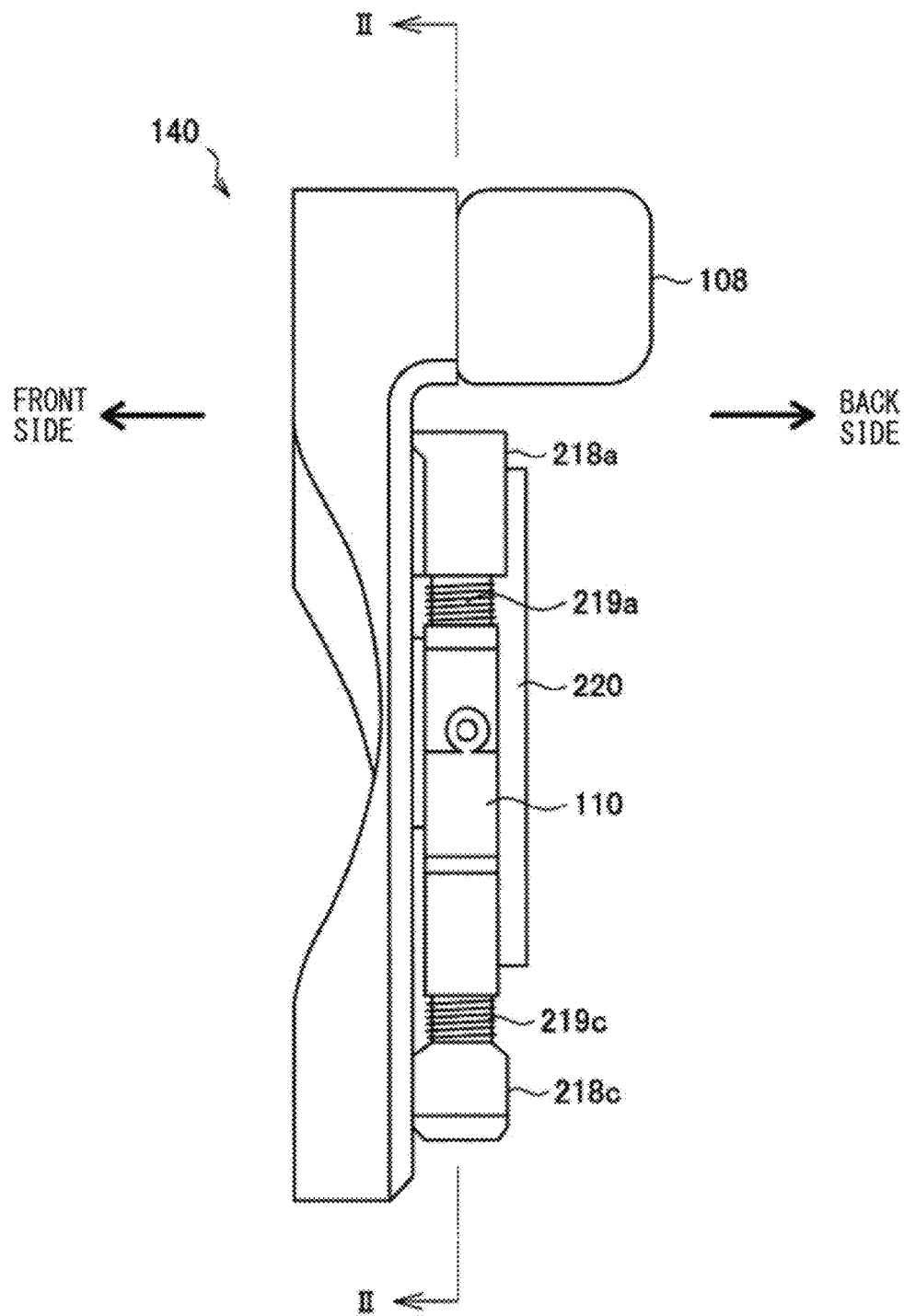
FIG. 18 is an explanatory diagram illustrating the first modification example according to the same embodiment.
Figure 19:
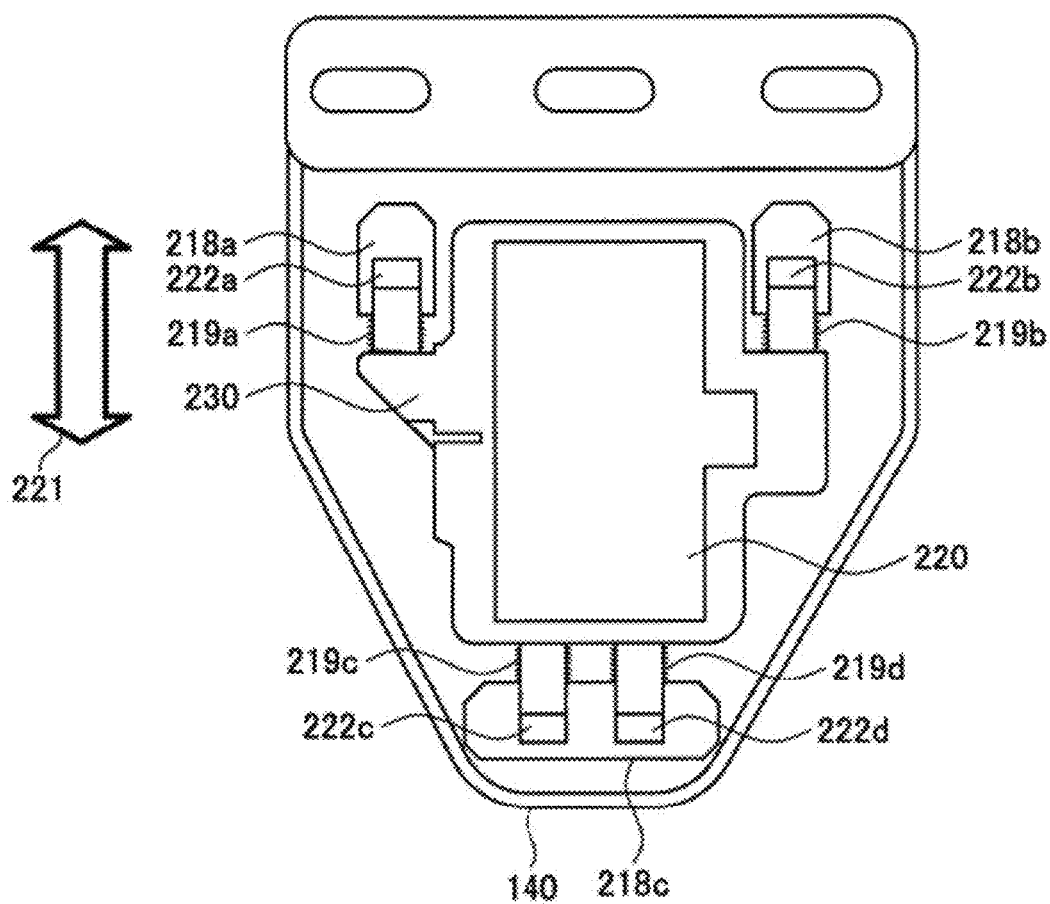
FIG. 19 is an explanatory diagram illustrating the first modification example according to the same embodiment.

Hereinafter, description is given of a first modification example according to the first embodiment of the present disclosure with reference to FIGS. 17 to 19. FIG. 17 is an explanatory diagram illustrating a first modification example according to the first embodiment of the present disclosure as viewed from the back side of the installation unit 140. FIG. 18 is an explanatory diagram illustrating the first modification example according to the first embodiment of the present disclosure as viewed from a side surface of the installation unit 140. FIG. 19 is an explanatory diagram illustrating a cross-section of the first modification example according to the first embodiment of the present disclosure along a cutting plane II. In the foregoing first embodiment, the description has been given of the example in which the VCM is used as the vibration unit 120; however, the LRA may be used as the vibration unit 120. Hereinafter, description is given of an example of assembling the tactile presentation apparatus in a case where the LRA is used as the vibration unit 120.

According to the foregoing first embodiment, as illustrated in FIG. 12, the VCM (vibration unit 120) vibrates in a direction (vibration direction 121) perpendicular to the first contact surface 111. Meanwhile, according to the present modification example, as illustrated in FIG. 17, the LRA (vibration unit 220) vibrates in a direction horizontal to the first contact surface 111. Specifically, the LRA vibrates in the direction of a vibration direction 221 illustrated in FIG. 17.

Due to such a difference in the vibration directions, as illustrated in FIG. 17, the shape of a contact unit 230 in the present modification example and the way the contact unit 230 is attached to the installation unit 140 differ from the foregoing first embodiment. For example, the contact unit 230 is attached to the installation unit 140 to allow the contact unit 230 to also vibrate in the vibration direction 221 when the vibration unit 220 vibrates in the vibration direction 221.

Specifically, the contact unit 230 is slidably attached to fixed parts 218 (fixed parts 218a, 218b, and 218c) of the installation unit 140 illustrated in FIG. 17 via springs 219 (springs 219a, 219b, 219c, and 219d). It is to be noted that, in the example illustrated in FIG. 17, the contact unit 230 is attached to the fixed part 218c by the two springs 219 (springs 219c and 219d).

Meanwhile, the installation unit 140 may be further provided with a fixed part [218d] by dividing the fixed part 218c to use the spring 219c for the fixed part 218c and to use the spring 219d for the fixed part.

In addition, even when the contact unit 230 vibrates in the direction of the vibration direction 221, predetermined spaces 222 (spaces 222a, 222b, 222c, and 222d) are secured inside the fixed parts 218 to allow the contact unit 230 and the fixed parts 218 to have no contact with each other. It is to be noted that the contact unit 230 and the fixed parts 218 are prevented from coming into contact with each other as long as the space 222 is secured to a distance exceeding at least the amplitude of the vibration unit 220 from the end of the contact unit 230 inside the fixed part 218.

As described above, even in a case of using a vibration device that vibrates in the horizontal direction with respect to the first contact surface 111, it is possible to implement the floating structure by modifying the shape of the contact unit 230 and the structure of attaching the contact unit 230 to the installation unit 140, to a structure according to the vibration direction of the vibration device.

(2) Second Modification Example

Figure 20:
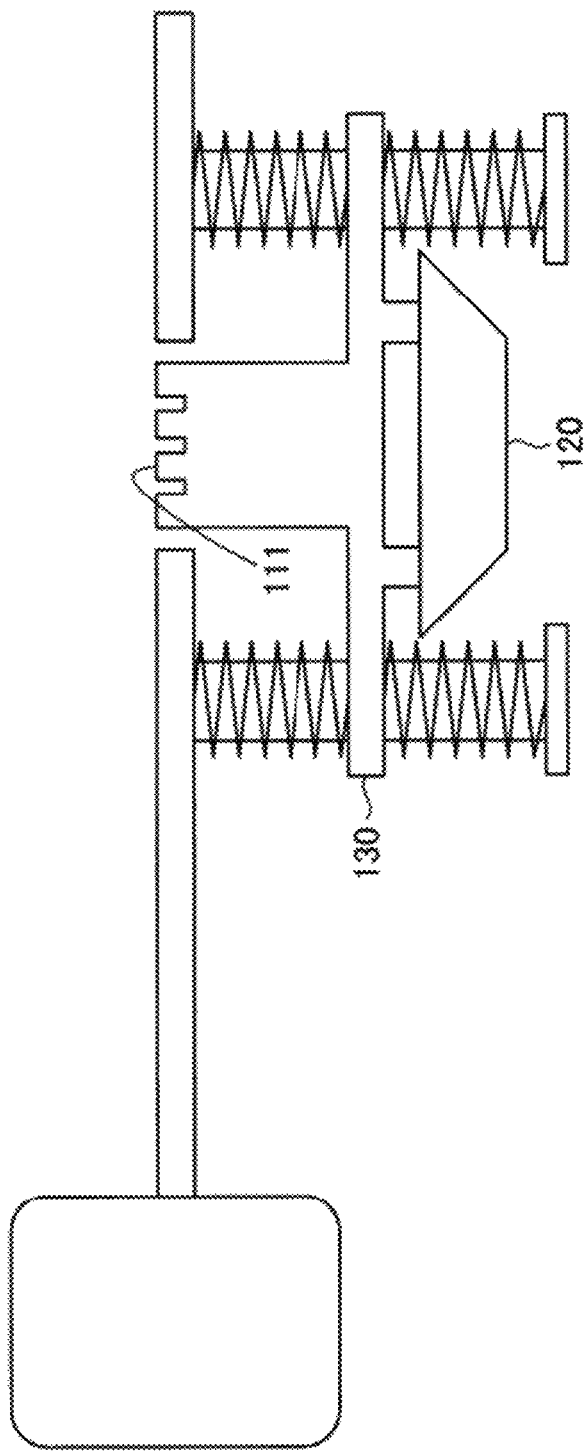
FIG. 20 is an explanatory diagram illustrating a second modification example according to the same embodiment.

Hereinafter, description is given of a second modification example according to the first embodiment of the present disclosure with reference to FIG. 20. FIG. 20 is an explanatory diagram illustrating the second modification example according to the first embodiment of the present disclosure. In the foregoing first embodiment, the description has been given of the case where the first contact surface 111 is flat; however, the first contact surface 111 may have concavity and convexity. For example, as illustrated in FIG. 20, the first contact surface 111 may have slits. The first contact surface 111 having the slits causes corners of the slits to come into contact with the finger of the user upon the vibration, and thus the user is able to sense vibration transmitted from the first contact surface 111 to the finger more sensitively than a case where the first contact surface 111 is flat.

The description has been given above, with reference to FIGS. 17 to 20, of the modification example according to the first embodiment of the present disclosure. Subsequently, description is given of a second embodiment of the present disclosure.

4. SECOND EMBODIMENT

In the first embodiment, the description has been given of an example of the interface operated by pressing the installation unit 140 of the operation apparatus 100; however, in the second embodiment, description is given of an example of an interface operated by rotating the operation unit of the operation apparatus. It is to be noted that a proximal side, as used in this section, refers to side (proximal end side) close to a coupling part between the operation apparatus and the body part of the master apparatus 10. In addition, a distal side refers to side (distal end side) distant from the coupling part between the operation apparatus and the body part of the master apparatus 10.

4.1. External Configuration Example of Operation Apparatus

Hereinafter, description is given of an external configuration example of an operation apparatus 300 according to the second embodiment of the present disclosure with reference to FIGS. 21 to 25.

<4.1.1. Overall Configuration Example>

Figure 21:
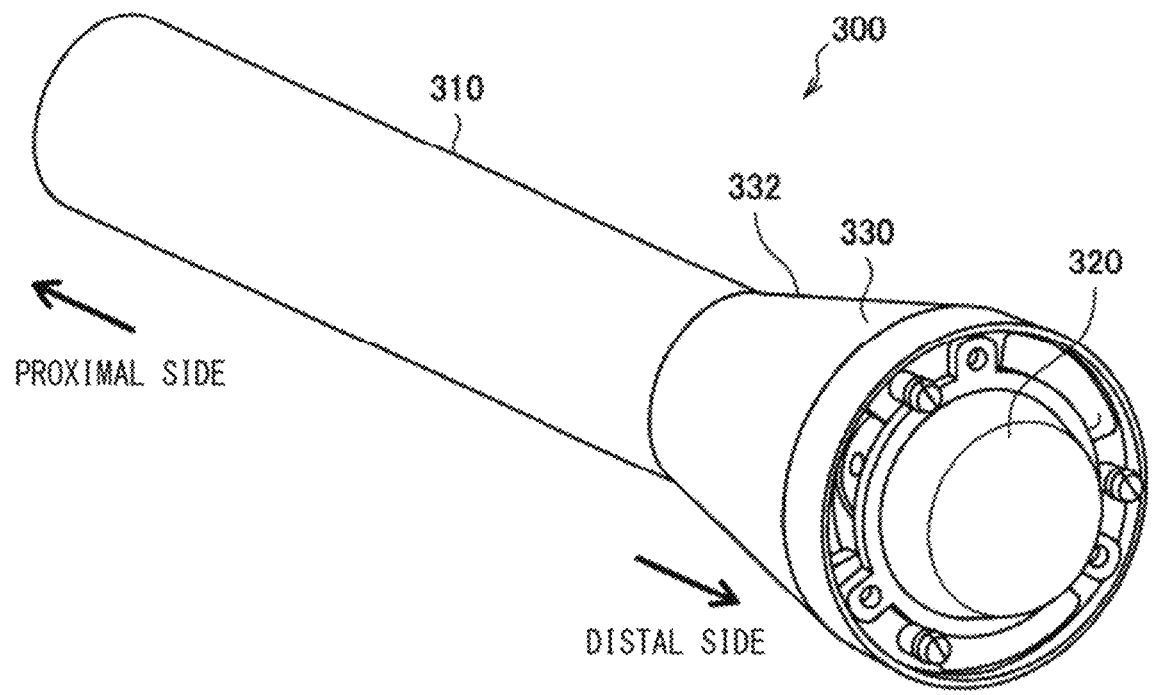
FIG. 21 is a perspective view of a tactile presentation apparatus according to a second embodiment of the present disclosure.
Figure 22:
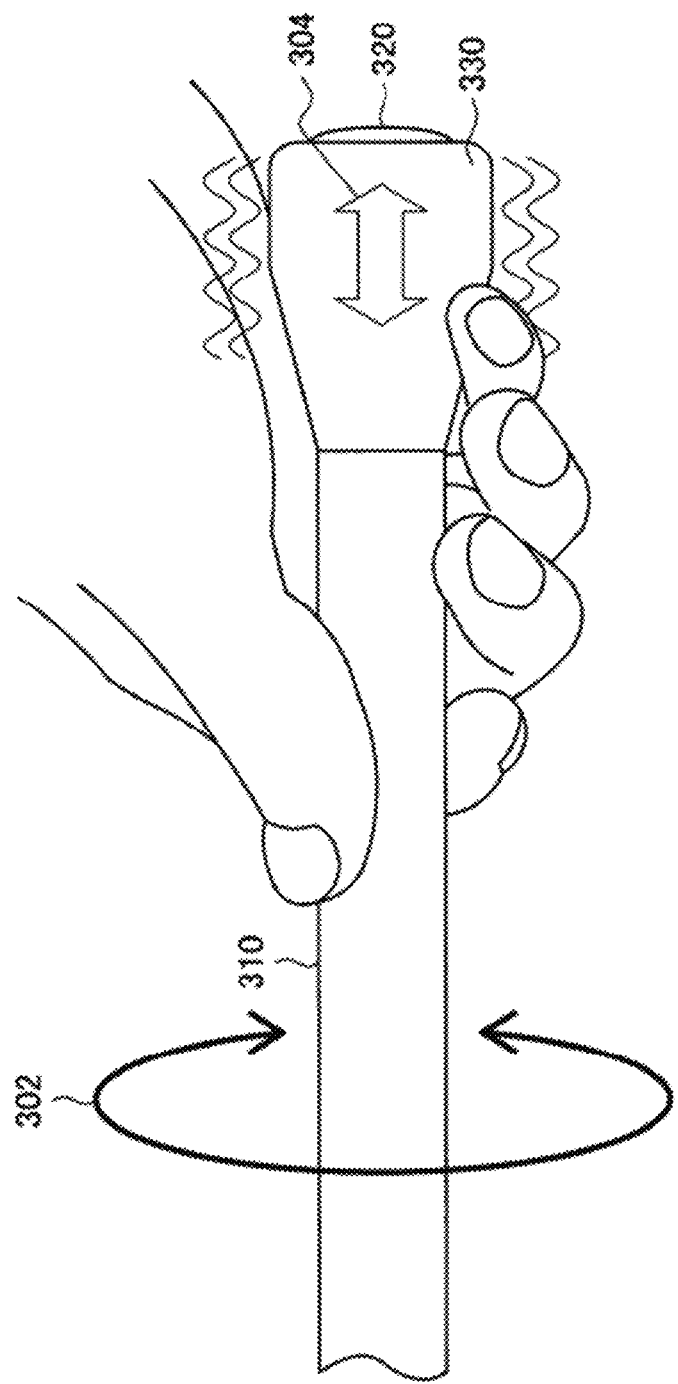
FIG. 22 is an explanatory diagram illustrating an operation example of the tactile presentation apparatus according to the same embodiment.

First, description is given of an overall configuration example of the operation apparatus 300 according to the second embodiment of the present disclosure with reference to FIGS. 21 and 22. FIG. 21 is a perspective view of a tactile presentation apparatus according to the second embodiment of the present disclosure. FIG. 22 is an explanatory diagram illustrating an operation example of the tactile presentation apparatus according to the second embodiment of the present disclosure.

An operation apparatus 300 illustrated in FIG. 21 includes an operation unit 310 that is able to accommodate, therein, a motor, a force sensor, or the like. The operation unit 310 has an elongated rod-like outer shape as a whole for easy grasping by a user. Such an operation apparatus 300 is attached to the fourth arm part 40d of the master apparatus 10 on the proximal side.

A contact unit 330 is provided on the distal side of the operation apparatus 300. The contact unit 330 is a unit with which a palm of the user comes into contact, and the outer circumferential surface of the contact unit 330 constitutes a third contact surface 332 with which the palm of the user comes into contact. The contact unit 330 is shaped such that the outer circumference on the distal side is larger than the outer circumference on the proximal side to allow the third contact surface 332 to be easily fit to the palm of the user when the user grasps the operation apparatus 300. Such a shape makes it possible for the user to stably grasp the contact unit 330 with the palm, a little finger, and the like. As a result, fingers not used for grasping are movable relatively freely, thus enabling the user to easily rotate the operation unit 310 with a thumb, an index finger, and the like, as described later. In the example illustrated in FIG. 22, the user grasps the contact unit 330 with the palm and a little finger to thereby support the entire operation apparatus 300, while putting other fingers on the operation unit 310, as illustrated in FIG. 22.

The operation apparatus 300 has a structure in which the operation unit 310 and the contact unit 330 are rotational in rotational directions 302 as illustrated in FIG. 22 independently of each other. Therefore, when the user grasps the operation apparatus 300 as described above, for example, the user moves the thumb and the index finger put on the operation unit 310 in directions opposite to each other to enable the operation unit 310 to rotate in any direction of the rotational directions 302 illustrated in FIG. 22.

In addition, the contact unit 330 is provided with the vibration unit 320. For example, a vibration unit 320 is provided on distal side of the contact unit 330. A vibration device is attached to the vibration unit 320 to vibrate in the direction of a vibration direction 304 illustrated in FIG. 22. In addition, when the vibration unit 320 vibrates, the contact unit 330 also vibrates, and thus the vibration of the vibration unit 320 is transmitted to the palm of the user via the third contact surface 332.

In a case where the operation apparatus 300 is mounted on the master apparatus 10, the vibration unit 320 generates a vibration corresponding to a tactile vibration acting on the surgical instrument of the slave apparatus 50, and the vibration is presented to the user via the third contact surface 332 of the contact unit 330.

It is to be noted that a wiring line such as a cable in the operation apparatus 300 may be wired inside the operation apparatus 300 or may be wired outside the operation apparatus 300, similarly to the operation apparatus 100 in the first embodiment.

The description has been given above, with reference to FIGS. 21 and 22, of the overall configuration example of the operation apparatus 300 according to the second embodiment of the present disclosure. Subsequently, description is given of a floating structure according to the second embodiment of the present disclosure.

<4.1.2. Configuration Example of Floating Structure Part>

Figure 23:
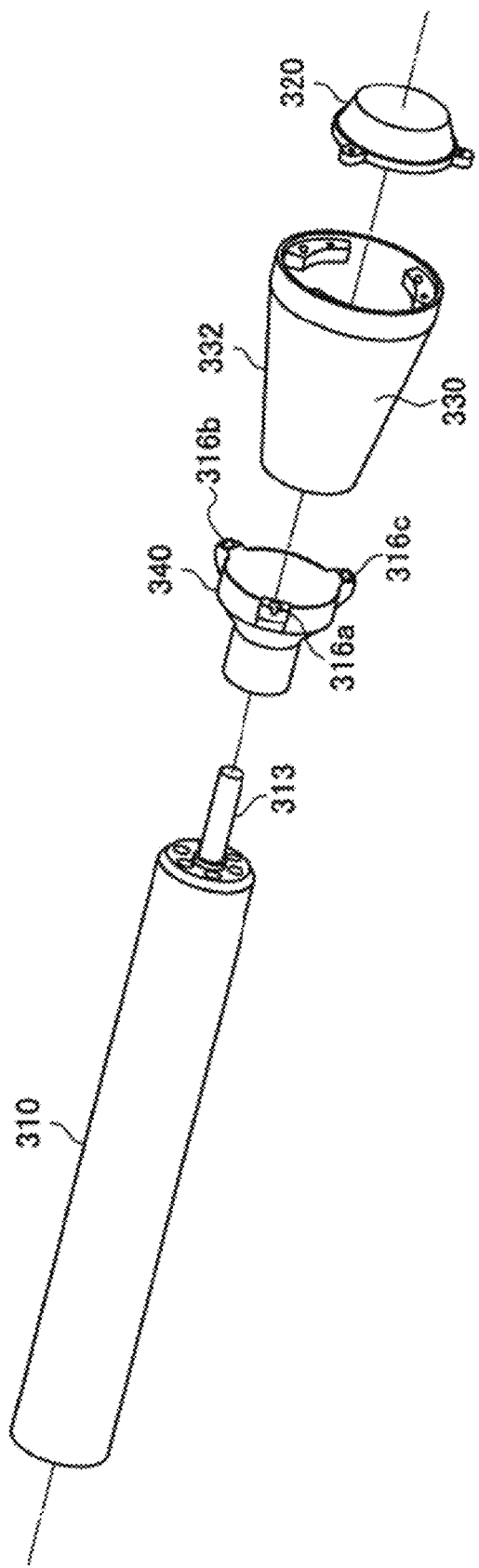
FIG. 23 is an explanatory diagram illustrating a partial configuration example of the tactile presentation apparatus according to the same embodiment.
Figure 24:
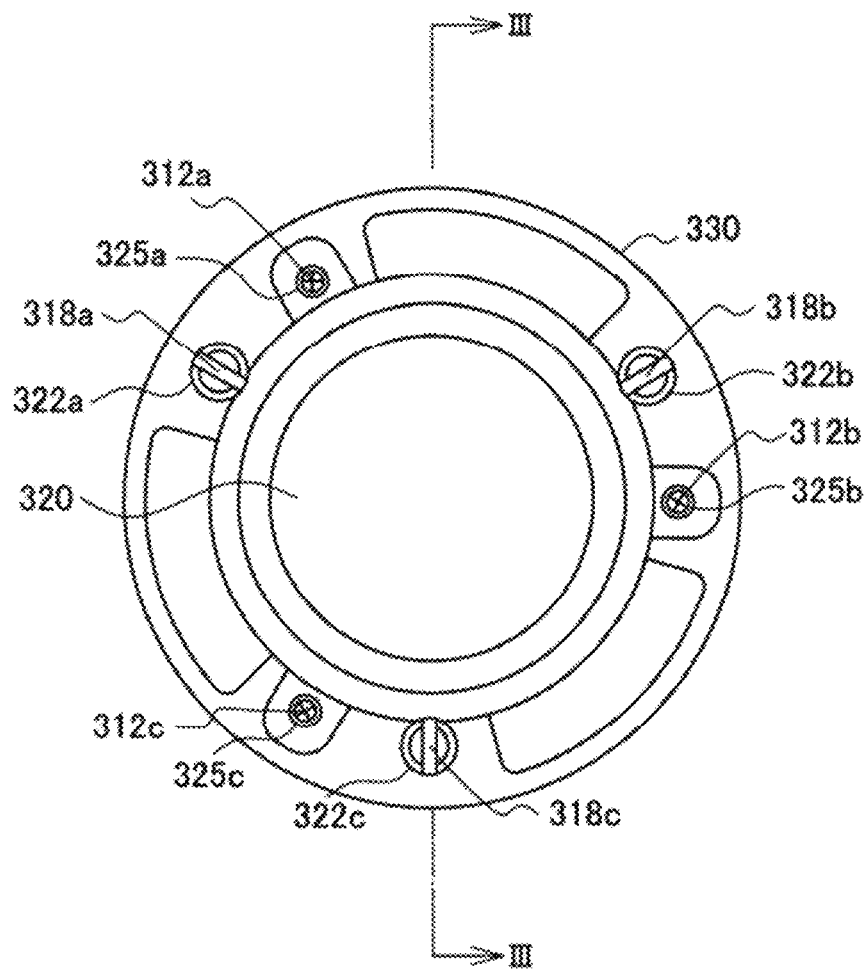
FIG. 24 is an explanatory diagram illustrating an example of assembling the tactile presentation apparatus according to the same embodiment.
Figure 25:
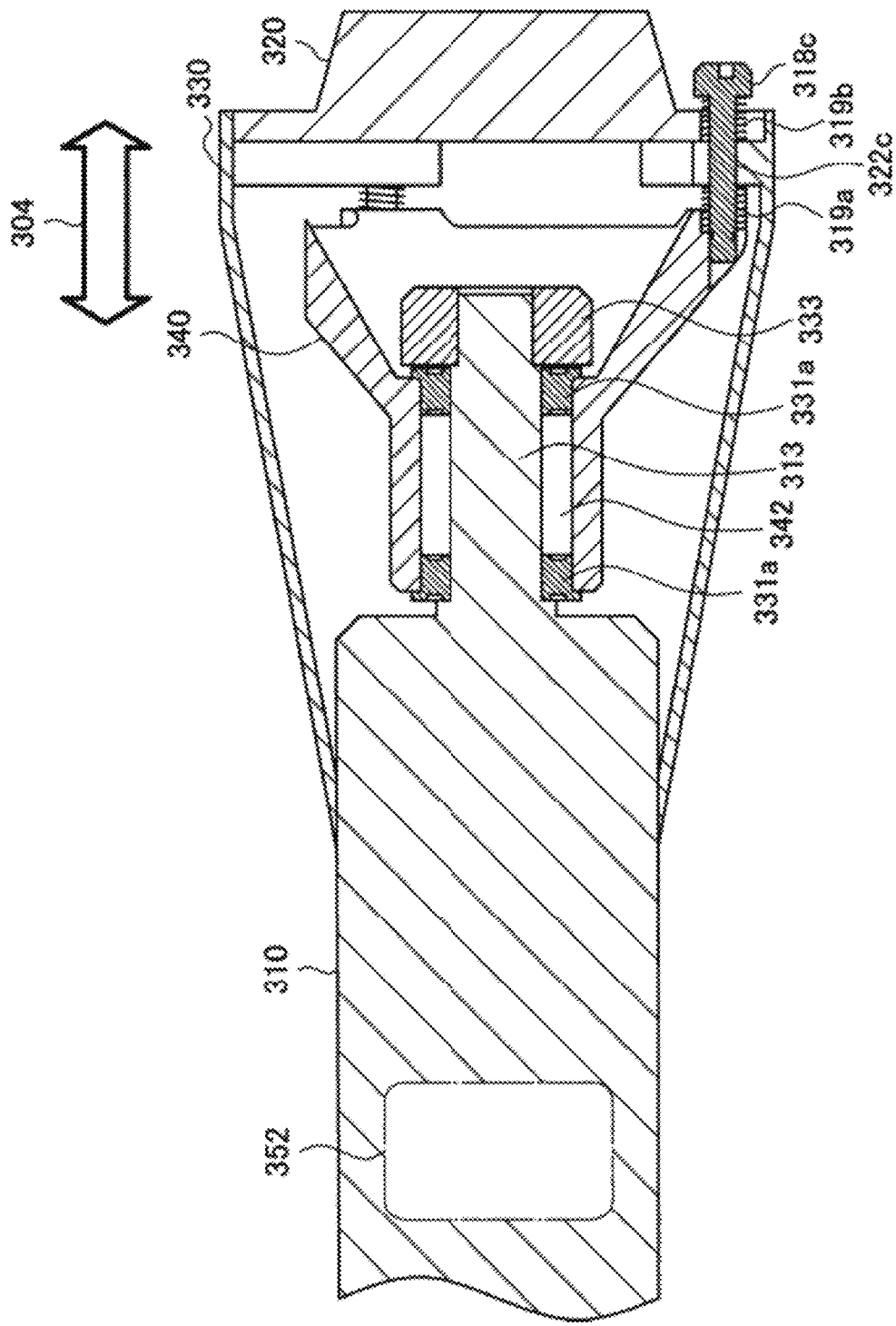
FIG. 25 is a cross-sectional view of a floating structure part of the tactile presentation apparatus according to the same embodiment.

Hereinafter, description is given of a configuration example of a floating structure part of the tactile presentation apparatus according to the second embodiment of the present disclosure with reference to FIGS. 23 to 25. FIG. 23 is an explanatory diagram illustrating a partial configuration example of the tactile presentation apparatus according to the second embodiment of the present disclosure. FIG. 24 is an explanatory diagram illustrating an example of assembling the tactile presentation apparatus according to the second embodiment of the present disclosure as viewed from distal side. FIG. 25 is a cross-sectional view of the floating structure part along a cutting line III of the tactile presentation apparatus according to the second embodiment of the present disclosure.

As illustrated in FIG. 23, the operation apparatus 300 according to the second embodiment of the present disclosure is roughly configured by four units. Specifically, the operation apparatus 300 is configured by the operation unit 310, the vibration unit 320, the contact unit 330, and an installation unit 340. The operation unit 310 includes, on the distal side, a shaft part 313 extending in a longitudinal direction of the operation unit 310. The installation unit 340 is provided rotatably along the shaft part 313 which is inserted thereinto. A direction in which the shaft part 313 extends, i.e., the longitudinal direction of the operation unit 310 is the direction of a rotational axis of the contact unit 330. It is to be noted that the operation unit 310 itself is also provided rotatably, with the longitudinal direction of the operation unit 310 as a rotational axis. That is, the rotational axes of the operation unit 310 and the contact unit 330 are the same. The inside of the contact unit 330 is a cavity, and has a tubular shape with openings at the end on the proximal side and at the end on the distal side. The installation unit 340, the contact unit 330, and the vibration unit 320 are fixed, with the installation unit 340 being contained in the inner space of the contact unit 330. The end on the distal side of the operation unit 310 is loosely inserted into an opening on the proximal side of the contact unit 330. In addition, the floating structure part according to the second embodiment of the present disclosure is configured by the vibration unit 320, the contact unit 330, and the installation unit 340. The floating structure according to the second embodiment of the present disclosure is a structure for suppressing transmission of the vibration generated by the vibration unit 320 to a force sensor 352.

It is to be noted that the operation apparatus 300 has a structure in which the vibration unit 320, the contact unit 330, and the installation unit 340 are provided on the distal side of the operation unit 310. This structure enables the user to stably grasp the operation apparatus 300 because of shifting of center of gravity of the operation apparatus 300 to the distal side which is grasped by the user. In addition, the user is able to stably grasp the operation apparatus 300, thus reducing shaking of the operation unit 310 on the proximal side at the time of grasping and operating the operation apparatus 300.

The operation unit 310 is a unit operated by the user in the operation apparatus 300. As illustrated in FIG. 25, the force sensor 352 is accommodated inside the operation unit 310.

When the user operates the operation unit 310, the force sensor 352 measures force of the user to be inputted to the operation unit 310.

The installation unit 340 is a unit that couples the operation unit 310 and the contact unit 330 to each other. As illustrated in FIG. 25, similarly to the contact unit 330, the installation unit 340 is shaped such that the outer circumference on the distal side is larger than an outer circumference on the proximal side. In addition, the installation unit 340 has an opening 342 that penetrates between the proximal side and the distal side. The shaft part 313 provided at the end on the distal side of the operation unit 310 is inserted into the opening 342. The operation unit 310 is coupled to the installation unit 340 via bearings 331 (bearings 331a). This enables the operation unit 310 and the installation unit 340 to be rotatable independently of each other in the rotational directions 302 illustrated in FIG. 22. Accordingly, the operation unit 310 and the contact unit 330 fixed to the installation unit 340 are rotatable independently of each other in the rotational directions 302 illustrated in FIG. 22. Meanwhile, a fixture 333 that covers and is fixed to the shaft part 313 is provided at the end on the distal side of the shaft part 313.

The fixture 333 prevents displacement of the installation unit 340 and the bearings 331 to the distal side.

The contact unit 330 is a unit that transmits the vibration generated by the vibration unit 320 to the user. The contact unit 330 has the third contact surface 332 to be in contact with the finger of the user. The contact unit 330 is able to transmit the vibration directly to the palm of the user through the third contact surface 332.

The contact unit 330 is slidably attached to distal side of the installation unit 340 along the longitudinal direction of the operation unit 310. Specifically, fixtures 318 (fixtures 318a, 318b, and 318c) having cross-sectional shapes smaller than those of holes 322 (holes 322a, 322b, and 322c) provided in the contact unit 330 are inserted into the holes 322 to allow the contact unit 330 to be slidably attached along the fixtures 318. Then, the fixtures 318 are fixed to holes 316 (holes 316a, 316b, and 316c) of the installation unit 340 illustrated in FIG. 23. Such a configuration enables the contact unit 330 to slide along the fixture 318 when vibrating together with the vibration unit 320.

Here, the contact unit 330 is attached to the installation unit 340 via an elastic body to have no direct contact with the installation unit 340. For example, as illustrated in FIG. 25, the contact unit 330 is attached to the installation unit 340 while being sandwiched by two springs 319 (springs 319a and 319b) which are elastic bodies, with respect to the hole 322c. More specifically, the spring 319a is mounted between the proximal side of the contact unit 330 and the distal side of the installation unit 340. In addition, the spring 319b is mounted between the distal side of the contact unit 330 and the head of the fixture 318c. The same applies to the unillustrated holes 322a and 322b. Such a configuration allows at least a portion of the vibration to be absorbed by the elastic body when the contact unit 330 and the vibration unit 320 vibrate together. Accordingly, it is possible to suppress the vibration transmitted from the contact unit 330 to the installation unit 340; as a result, it is also possible to suppress the vibration transmitted to the force sensor 352 via the operation unit 310 to which the installation unit 340 is attached.

The fixture 318 is inserted into space inside the spring 319. This allows a direction in which the spring 319 expands and contracts and a sliding direction of the contact unit 330 to coincide with each other, thus making it possible to fix the sliding direction of the contact unit 330 to one axis.

As described above, the structure in which the contact unit 330 is attached to the installation unit 340 via the elastic body, with the contact unit 330 and the installation unit 340 being in non-contact is referred to as the floating structure. It is to be noted that an elastic body other than the spring may be used to implement the floating structure. For example, a spring damper may be used instead of the spring. In addition, a rigidity variable mechanism that is able to vary the rigidity may be adopted for the floating structure to thereby enable the rigidity of the elastic body to be variable. In addition, the contact unit 330 attached to the installation unit 340 via the elastic body allows the contact unit 330 and the operation unit 310 to be in non-contact, thus causing the contact unit 330 and the operation unit 310 to be separated from each other.

In addition, as described above, the operation apparatus 300 has a structure in which the operation unit 310 is coupled to the installation unit 340 via the bearing 331, with the contact unit 330 being attached to the installation unit 340. This structure allows the operation unit 310 to be rotatable along a predetermined rotational axis and allows the contact unit 330 to be rotatable along the predetermined rotational axis independently of the operation unit 310. In addition, the operation unit 310 rotates independently of the contact unit 330, whereby the position at which the contact unit 330 comes into contact with the palm of the user does not change even when the user rotates the operation unit 310. Accordingly, a vibration is presented at a certain position of the palm from the contact unit 330, and thus the user is more likely to sense a change in intensity of the vibration than a case where the contact position is converted.

In addition, the operation unit 310 is rotatable by plus or minus 180 degrees or more from a reference state. The reference state, as used herein, refers to an initial state in which the user grasps the contact unit 330 with the palm and the little finger while putting other fingers on the operation unit 310. It is desirable for the operation unit 310 to be rotatable by equal to or more than an angle at which the user is able to rotate the operation unit 310 without changing the grip of the operation unit 310. Accordingly, it is desirable for the operation unit 310 to be rotatable by 90 degrees or more from the reference state. In addition, it is also desirable for the operation unit 310 to allow an operation of the user to change the grip and rotate the operation unit 310 again in the same direction. Accordingly, it is desirable for the operation unit 310 to be rotatable by 180 degrees or more from the reference state. Thus, the operation unit 310 is rotatable by 180 degrees or more from the reference state, thereby making it possible to achieve the above-described operation without changing the grip of the operation unit 310.

In addition, the cylindrical shape of the operation unit 310 enables the user to obtain the same operational feeling at each grasped location even when the user grasps anywhere on the operation unit 310. In addition, the user does not need to change the grip of the operation unit 310 each time when performing an operation. In addition, the frusto-conical shape of the contact unit 330 enables the user to obtain effects similar to those of the cylindrical shape of the operation unit 310 described above.

It is to be noted that, in order to obtain the effects described above, the shape of the cross-section orthogonal to the rotational axis direction of the operation unit 310 is desirably circular; however, a shape other than circular may also be adopted as long as the operation unit 310 has a rotatable shape. For example, the cross-sectional shape orthogonal to the rotational axis direction of the operation unit 310 may be polygonal. In addition, the diameter of the cross-section is not particularly limited, but is desirably a diameter that is realistically easy to be handled by a human hand.

In addition, a component other than the bearing may be used to achieve the above-described structures in which the operation unit 310 and the contact unit 330 rotate independently of each other. For example, a bush may be used instead of the bearing.

The vibration unit 320 is provided on the distal side of the contact unit 330. Specifically, as illustrated in FIG. 24, screws 312 (screws 312*a*, 312*b*, and 312*c*) penetrate holes 325 (holes 325*a*, 325*b*, and 325*c*) of the vibration unit 320 from the distal side thereof. Then, the screws 312 are fixed to screw holes 326 (screw holes 326*a*, 326*b*, and 326*c*) of the contact unit 330. In this manner, the vibration unit 320 is fixedly attached to the distal side of the contact unit 330.

In addition, the vibration unit 320 vibrates in a direction in which the elastic body expands and contracts and in a direction corresponding to the direction of the predetermined rotational axis. For example, the vibration unit 320 vibrates in a direction coincident or substantially coincident with the direction in which the elastic body expands and contracts. Specifically, the vibration unit 320 vibrates in the direction of the vibration direction 304 illustrated in FIG. 25. The vibration direction 304 coincides with directions in which the springs 319*a* and 319*b* expand and contract, which are elastic bodies illustrated in FIG. 25. In addition, the vibration direction 304 also coincides with the rotational axis direction of the operation unit 310. Typically, the elastic body exhibits higher vibration absorbing capacity as direction of the force applied to the elastic body more coincides with the direction of expansion and contraction. Accordingly, the vibration unit 320 vibrates in a direction coincident or substantially coincident with the direction in which the elastic body expands and contracts, thereby enabling the elastic body to efficiently absorb the vibration generated by the vibration unit 320. In addition, the vibration direction of the vibration unit 320 and the rotational axis direction of the operation unit 310 coincide with each other, thereby enabling the contact unit 330 to provide the same vibration to the user in each state regardless of the rotational states of the operation unit 310 or the contact unit 330. In addition, the vibration direction of the vibration unit 320 and the rotational axis direction of the operation unit 310 coincide with each other, thereby enabling the contact unit 330 to provide the same operational feeling in each state regardless of the way the user holds the operation unit 310.

Here, summarizing the above description, the contact unit 330 is provided with the vibration unit 320. The installation unit 340 is provided with the contact unit 330 via the elastic body. Then, the installation unit 340 is provided to the operation unit 310. Thus, when the vibration unit 320 vibrates, the vibration generated from the vibration unit 320 is transmitted to the contact unit 330, and the contact unit 330 also vibrates together. Further, in a case where a portion of the body of the user, e.g., the palm of the user comes into contact with the third contact surface 332 of the contact unit 330, the vibration generated from the contact unit 330 is transmitted to the palm or the finger of the user via the third contact surface 332.

In addition, the contact unit 330 is slidably fixed to the installation unit 340 by the fixture 318 via the spring 319. Accordingly, at least a portion of the vibration is absorbed by the elastic body when the contact unit 330 and the vibration unit 320 vibrate together. Accordingly, it is possible to suppress the vibration transmitted from the contact unit 330 to the installation unit 340; as a result, it is also possible to suppress the vibration transmitted to the force sensor 352 via the operation unit 310 to which the installation unit 340 is attached.

It is to be noted that, as described above, when the vibration unit 320 vibrates, the contact unit 330 also vibrates together. That is, it can also be said that the vibration unit 320 vibrates the contact unit 330. At this time, it is necessary to have an output according to the mass of the contact unit 330; therefore, as the mass of the contact unit 330 becomes larger, the vibration unit 320 needs to have a larger output, which accordingly results also in an increased size of the vibration device used for the vibration unit 320. Therefore, in order to avoid the increased size of the vibration device, it is desirable to use a lightweight material for the material of the contact unit 330. For example, use of a POM (PolyOxyMethylene) resin makes it possible to reduce the weight of the contact unit 330.

The description has been given above, with reference to FIGS. 23 to 25, of the configuration example of the floating structure part of the tactile presentation apparatus according to the second embodiment of the present disclosure.

The description has been given above, with reference to FIGS. 20 to 25, of the external configuration example of the operation apparatus 300 according to the second embodiment of the present disclosure. Subsequently, description is given of an operation example according to the second embodiment of the present disclosure.

4.2. Operation Example

The operation of a signal processor according to the second embodiment of the present disclosure is the same as the operation of the signal processor 170 according to the first embodiment of the present disclosure, which has been described in <3.2. Operation Example>, and thus description in this section is omitted to avoid repeated description. Consequently, description is given of modification examples according to the second embodiment of the present disclosure.

4.3. Modification Examples

Hereinafter, description is given of modification examples according to the second embodiment of the present disclosure with reference to FIGS. 26 to 28. It is to be noted that the modification examples described below may be applied alone to the second embodiment of the present disclosure or may be applied in combination to the second embodiment of the present disclosure. In addition, the modification example may be applied in place of the configuration described in the second embodiment of the present disclosure, or may be applied additionally to the configuration described in the second embodiment of the present disclosure.

(1) First Modification Example

Hereinafter, description is given of a first modification example according to the second embodiment of the present disclosure with reference to FIG. 26. FIG. 26 is an explanatory diagram illustrating the first modification example according to the second embodiment of the present disclosure. In the foregoing second embodiment, the description has been given of an example in which the operation apparatus 300 is attached to the tip end of the parallel link mechanism; however, the operation apparatus 300 may be attached to the tip end of a support rest 337 and a uniaxial slider 339 as illustrated in FIG. 26. In the structure illustrated in FIG. 26, the user is able to slide the operation apparatus 300 together with the support rest 337 in the direction of a moving direction 338 (i.e., the proximal direction or the distal direction). In addition, the user is able to rotate the operation unit 310 in a rotational direction 334.

The above-described structure is applicable, for example, to the master apparatus 10 in a case of performing an insertion operation of a catheter. Specifically, when the user slides the operation apparatus 300 in the moving direction 338, a corresponding device on the side of the slave apparatus 50 performs the operation of inserting the catheter. In addition, when the user rotates the operation unit 310 in the rotational direction 334, the corresponding device on the side of the slave apparatus 50 is able to rotatably change the orientation of the catheter. In addition, the operation apparatus 300 is also able to transmit to the user a feedback from the operation of a device on the side of the slave apparatus 50. For example, when receiving a feedback from the slave apparatus 50, a motor 335 of the operation apparatus 300 is driven on the basis of the feedback, thereby making it possible to transmit a feedback to the user, such as sliding the support rest 337 or rotating the operation unit 310.

In addition, the above-described structure may be applied to a game machine operable simply by sliding or rotating.

(2) Second Modification Example

Hereinafter, description is given of a second modification example according to the second embodiment of the present disclosure with reference to FIG. 27. FIG. 27 is an explanatory diagram illustrating the second modification example according to the second embodiment of the present disclosure. In the foregoing second embodiment, the description has been given such that the wiring line such as a cable in the operation apparatus 300 may be wired either inside or outside the operation apparatus 300. For example, in a case where wiring lines of the vibration unit 320 and the operation unit 310 are wired inside the operation apparatus 300, the wiring lines inside the vibration unit 320 and the operation unit 310 may be electrically coupled via a slip ring. Specifically, as illustrated in FIG. 27, the slip ring 341 is provided between the proximal side of the contact unit 330 and the distal side of the installation unit 340. Then, the slip ring 341 and the vibration unit 320 are electrically coupled by a cable 343a. In addition, a cable 343b extended out of the slip ring 341 is passed through an opening 314 provided in the operation unit 310. In addition, a force sensor 352 having an opening that penetrates between proximal side and distal side may be used for the force sensor 352. The use of such a force sensor 352 enables the opening 314 to pass through the inside of the opening of the force sensor 352 as illustrated in FIG. 27, thus making it possible to easily wire the cable 343b to the proximal side of the force sensor 352.

As described above, the wiring lines inside the vibration unit 320 and the operation unit 310 are electrically coupled via the slip ring, whereby the internal cable is not entangled even when the operation unit 310 rotates, thus making it possible to avoid entangling of the internal cable due to rotation and thus to avoid breaking of the cable.

(3) Third Modification Example

Hereinafter, description is given of a third modification example according to the second embodiment of the present disclosure with reference to FIG. 28. FIG. 28 is an explanatory diagram illustrating third and fourth modification examples according to the second embodiment of the present disclosure. In the foregoing second embodiment, the shape of the third contact surface 332 of the contact unit 330 is not explicitly specified; however, the third contact surface 332 may have a protruded part protruded along a rotational direction of the contact unit 330 or a recessed part recessed along the rotational direction of the contact unit 330. For example, as illustrated in FIG. 28, the third contact surface 332 has a protruded part 345 protruded along the rotational direction of the contact unit 330. In addition, the portion of the protruded part 345 may be a recessed part recessed along the rotational direction of the contact unit 330. In addition, a polygonal shape may be adopted for the cross-section of the contact unit 330 orthogonal to the rotational axis direction of the contact unit 330 to thereby provide the third contact surface 332 with the protruded part or the recessed part.

As described above, the third contact surface 332 provided with the protruded part that is protruded or the recessed part that is recessed along the rotational direction of the contact unit 330 enables the user to hook fingers onto the protruded part or into the recessed part when grasping the operation apparatus 300. Thus, it is possible for the protruded part or the recessed part to improve stability at the time when the user grasps the operation apparatus 300.

(4) Fourth Modification Example

Hereinafter, description is given of a fourth modification example according to the second embodiment of the present disclosure with reference to FIG. 28. FIG. 28 is an explanatory diagram illustrating the third and fourth modification examples according to the second embodiment of the present disclosure. In the foregoing second embodiment, the type and the position of the force sensor 352 provided inside the operation unit 310 are not explicitly specified.

The type of the force sensor 352 may include, for example, a multi-axis force sensor. More specifically, a six-axis force sensor may be used as the multi-axis force sensor. Providing the six-axis force sensor inside the operation unit 310 allows the six-axis force sensor to detect translational force and moment at the time when the user moves the operation apparatus 300.

Figure 28:
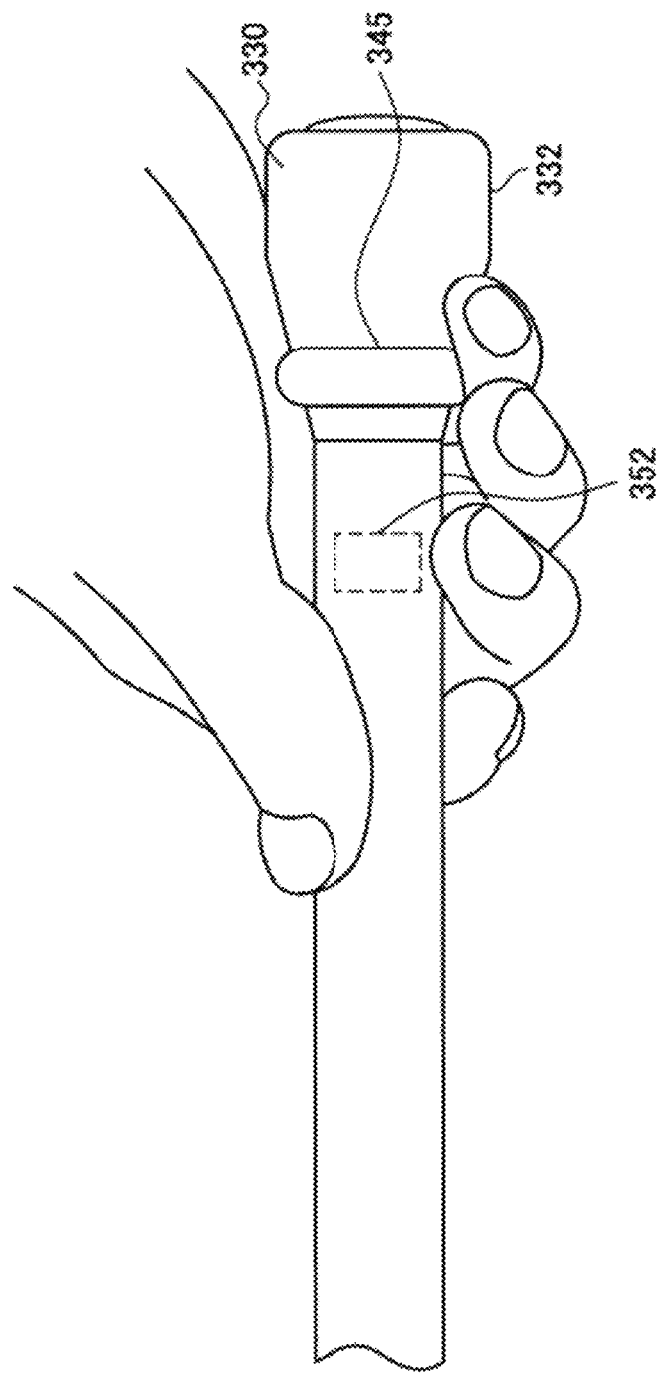
FIG. 28 is a cross-sectional view of third and fourth modification examples according to the same embodiment.

In addition, when the user grasps the operation apparatus 300, the force sensor 352 is desirably positioned in the vicinity of the middle inside the hand of the user, as illustrated in FIG. 28. One reason for this is that, in a case where the force sensor 352, which is able to detect moment, such as the above-described six-axis force sensor is provided at the end on the proximal side of the operation unit 310, excessive moment acts on slight translational force, which may possibly make the force sensor 352 more likely to be fragile. Generally, the magnitude of moment at a certain position is proportional to a distance from a fulcrum. When setting, as the fulcrum, the vicinity of the middle inside the hand at the time when the user grasps the operation apparatus 300, the farther the position of the force sensor 352 moves away from the fulcrum to the end on the proximal side of the operation unit 310, the larger a distance between the fulcrum and the force sensor 352 becomes, thus causing the magnitude of the moment to be greater. Therefore, by providing the force sensor 352 in the vicinity of the middle inside the hand of the user, which is the fulcrum, the distance between the force sensor 352 and the fulcrum is decreased, and the magnitude of the moment is also reduced, thus making translational force less likely to act as moment.

As described above, providing the force sensor 352 in the vicinity of the middle of the hand of the user suppresses generation of excessive moment, thus preventing damage to the force sensor 352 and enhancing sensing sensitivity.

Figure 26:
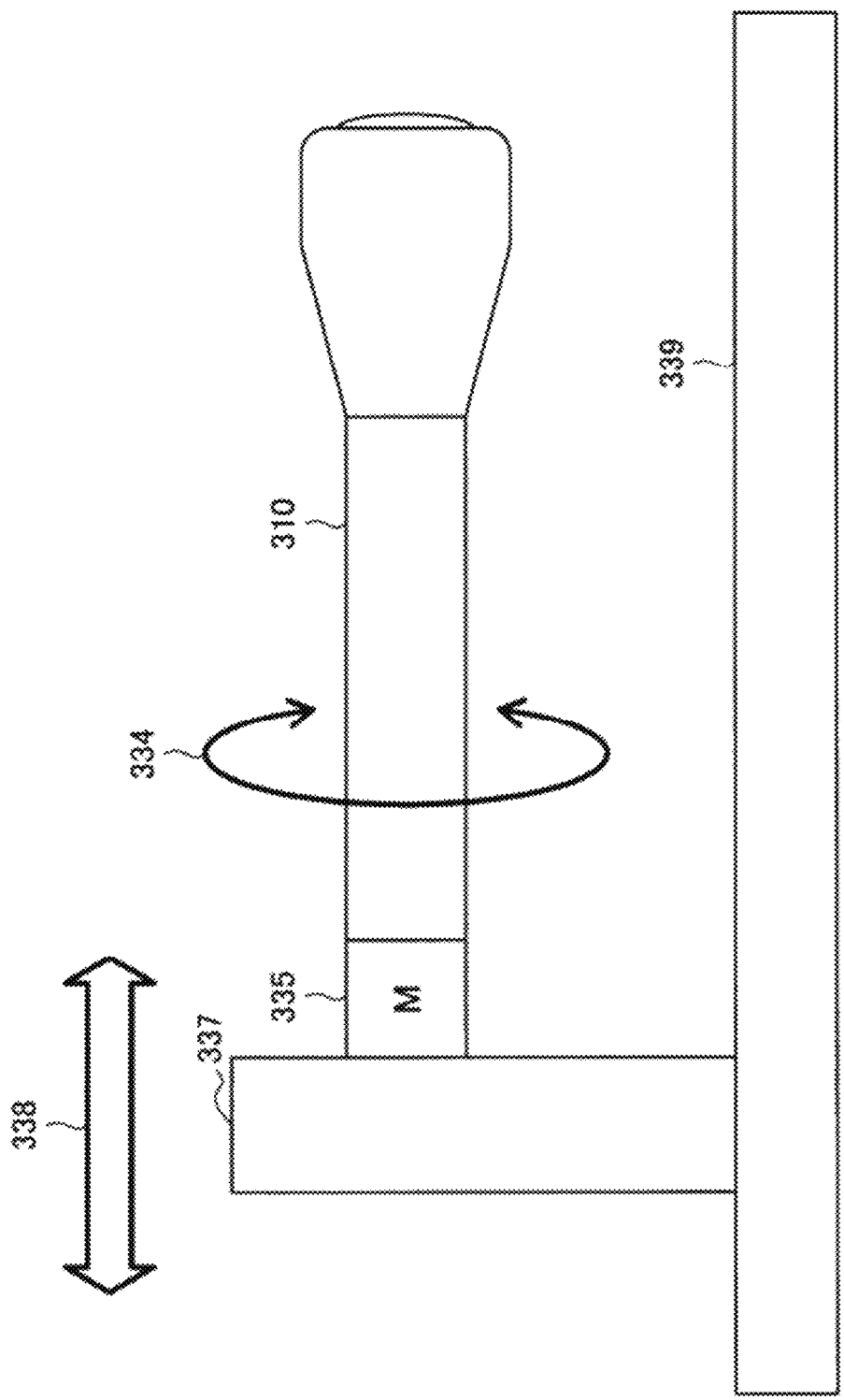
FIG. 26 is an explanatory diagram illustrating a first modification example according to the same embodiment.
Figure 27:
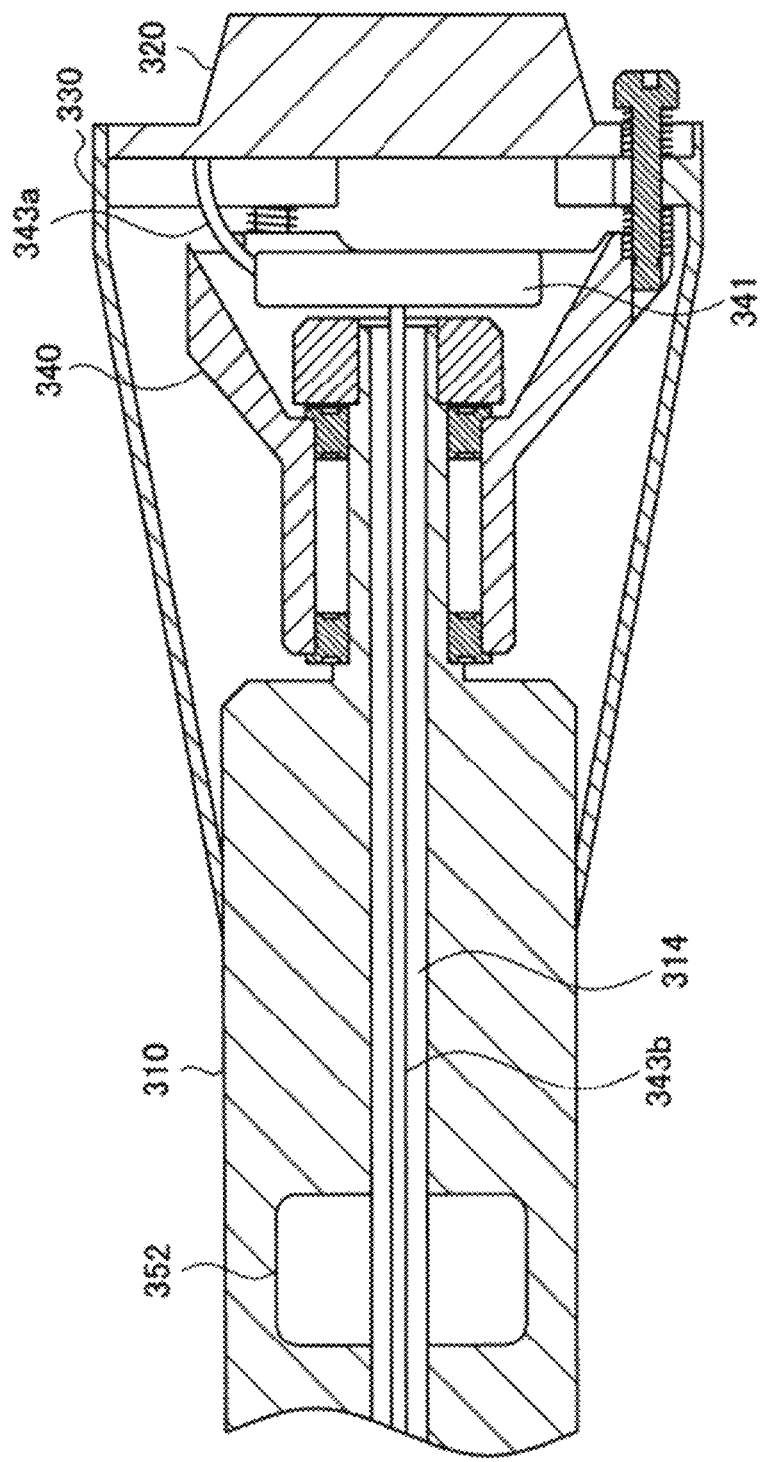
FIG. 27 is a cross-sectional view of a second modification example according to the same embodiment.

The description has been given above, with reference to FIGS. 26 to 28, of the modification examples according to the second embodiment of the present disclosure. Subsequently, description is given of a hardware configuration example of the tactile presentation apparatus according to an embodiment of the present disclosure.

5. HARDWARE CONFIGURATION

Lastly, description is given of a hardware configuration of the master apparatus according to an embodiment of the present disclosure with reference to FIG. 29. FIG. 29 is a block diagram illustrating an example of the hardware configuration of the master apparatus 10 according to an embodiment of the present disclosure. Information processing by the master apparatus 10 according to an embodiment of the present disclosure is implemented by cooperation of software and hardware described below.

The master apparatus 10 includes a CPU (Central Processing Unit) 901, a ROM (Read Only Memory) 903, and a RAM (Random Access Memory) 905. In addition, the master apparatus 10 includes an input device 907, a storage device 909, and a communication device 911.

The CPU 901 functions as an arithmetic processing device and a control device, and controls overall operations inside the master apparatus 10 in accordance with various programs. In addition, the CPU 901 may be a microprocessor. The ROM 903 stores programs to be used by the CPU 901, arithmetic parameters, and the like. The RAM 905 temporarily stores programs to be used in execution by the CPU 901, parameters that vary appropriately in executing the programs, and the like. These components are coupled mutually by a host bus configured by a CPU bus, or the like. The CPU 901, the ROM 903 and the RAM 905 may implement the functions of the signal processor 170 described with reference to FIG. 3, for example.

The input device 907 is configured by input means for the user to input information such as a touch panel, a button, a camera, a microphone, a sensor, a switch and a lever, and an input control circuit to generate an input signal on the basis of an input by a user and to output the generated input signal to the CPU 901. For example, the user controls the master apparatus 10 to cause the slave apparatus 50 to operate, whereby the input device 907 acquires data to thereby input various data to the slave apparatus 50 or instruct the slave apparatus 50 to perform a processing operation. The input device 907 may implement the functions of the sensor unit 150 described with reference to FIG. 3, for example.

The storage device 909 is a device for storing data. The storage device 909 may include a storage medium, a recording device that records data on the storage medium, a reading device that reads data from the storage medium, and a deleting device that deletes data recorded on the storage medium. The storage device 909 is configured by, for example, an HDD (Hard Disk Drive) or an SSD (Solid Strage Drive), or by a memory having equivalent functions. The storage device 909 drives the storage, and stores programs to be executed by the CPU 901 and various data. The storage device 909 may implement the functions of the storage section 180 described with reference to FIG. 3, for example.

The communication device 911 is, for example, a communication interface configured by a communication device, etc. for coupling the master apparatus 10 and the slave apparatus 50 to each other. Such a communication interface is, for example, a short-range wireless communication interface such as Bluetooth (registered trademark) or ZigBee (registered trademark), or a communication interface such as wireless LAN (Local Area Network), Wi-Fi (registered trademark) or a mobile communication network (LTE, 3G). In addition, the communication device 911 may be a wired communication device that performs wired communication.

The description has been given above of the hardware configuration of the master apparatus 10 with reference to FIG. 29.

6. CONCLUSION

As described above, the tactile presentation apparatus according to the present disclosure includes the operation unit operated by the user, the vibration unit that presents a vibration of an operation target of the operation unit, the contact unit that transmits the vibration to the user, and the installation unit that couples the contact unit and the operation unit to each other. In addition, the tactile presentation apparatus has a configuration in which the vibration unit is attached to the contact unit, the contact unit is attached to the installation unit via the elastic body, and the installation unit is attached to the operation unit.

Such a configuration enables the tactile presentation apparatus to transmit a vibration generated from the vibration unit to the user via the contact unit and to cause the elastic body to reduce transmission of the vibration to the force sensor provided in the master apparatus. Thus, it is possible to provide the novel and improved tactile presentation apparatus and tactile presentation system that make it possible to reduce a noise to be transmitted to the force sensor.

Although the description has been given above in detail of preferred embodiments of the present disclosure with reference to the accompanying drawings, the technical scope of the present disclosure is not limited to such examples. It is obvious that a person having ordinary skill in the art of the present disclosure may find various alterations or modifications within the scope of the technical idea described in the claims, and it should be understood that these alterations and modifications naturally come under the technical scope of the present disclosure.

In addition, the processing described herein with reference to a flowchart and a sequence diagram may not necessarily be executed in the illustrated order. Several processing steps may be executed in parallel. In addition, an additional processing step may be employed, or some of the processing steps may be omitted.

In addition, the effects described herein are merely illustrative or exemplary, and are not limitative. That is, the technology according to the present disclosure may achieve, in addition to or in place of the above effects, other effects that are obvious to those skilled in the art from the description of the present specification It is to be noted that the technical scope of the present disclosure also includes the following configurations (1)

A tactile presentation apparatus including:
an operation unit operated by a user;
a vibration unit that presents a vibration of an operation target of the operation unit;
a contact unit that transmits the vibration by the vibration unit to the user; and
an installation unit coupled to the operation unit, over the contact unit provided via an elastic body.

(2)

The tactile presentation apparatus according to (1), in which the contact unit has a first contact surface to be in contact with a finger of the user, and the vibration unit transmits the vibration to the finger of the user via the first contact surface.

(3)

The tactile presentation apparatus according to (2), in which the installation unit has a second contact surface with which the finger of the user comes into contact and an opening that penetrates between side of the second contact surface and back side of the second contact surface, and the contact unit is provided to be inserted through the opening from the back side of the second contact surface.

(4)

The tactile presentation apparatus according to (3), in which the first contact surface and the second contact surface coincide or substantially coincide with each other in a vibration direction of the vibration unit, with the vibration unit being stopped.

(5)

The tactile presentation apparatus according to (4), in which the shortest distance in the vibration direction between the first contact surface and an end of the second contact surface that forms the opening is within a range of a value corresponding to amplitude of the vibration unit.

(6)

The tactile presentation apparatus according to any one of (1) to (5), in which the vibration unit vibrates in a direction corresponding to a direction in which the elastic body expands and contracts.

(7)

The tactile presentation apparatus according to (6), in which the vibration unit vibrates in a direction coincident or substantially coincident with the direction in which the elastic body expands and contracts.

(8)

The tactile presentation apparatus according to any one of (2) to (5), in which the first contact surface has concavity and convexity.

(9)

The tactile presentation apparatus according to any one of (1) to (8), in which the tactile presentation apparatus further includes a force sensor that measures force inputted to the operation unit, and a signal processor that removes a component of the vibration presented by the vibration unit from the force measured by the force sensor.

(10)

The tactile presentation apparatus according to (9), in which the signal processor reduces an influence of a vibration noise correlated with force of the user by using an adaptive filter for the vibration.

(11)

The tactile presentation apparatus according to (9) or (10), in which the signal processor corrects the force of the user measured by the force sensor by inverse dynamics computation.

(12)

The tactile presentation apparatus according to (9), in which the signal processor uses a filter to remove, from the vibration, a frequency component other than a frequency component corresponding to a human tactile sense or a predetermined frequency component stored in advance.

(13)

The tactile presentation apparatus according to (1), in which the operation unit is rotatable along a predetermined rotational axis, and the contact unit is rotatable along the predetermined rotational axis independently of the operation unit.

(14)

The tactile presentation apparatus according to (13), in which the vibration unit vibrates in a direction corresponding to a direction of the predetermined rotational axis.

(15)

The tactile presentation apparatus according to (13) or (14), in which the vibration unit, the contact unit, and the installation unit are provided on distal end side of the operation unit.

(16)

The tactile presentation apparatus according to any one of (13) to (15), in which an outer circumferential surface of the contact unit constitutes a third contact surface, and the vibration unit transmits the vibration to the user via the third contact surface.

(17)

The tactile presentation apparatus according to (16), in which an outer circumference on distal end side of the contact unit is larger than an outer circumference on proximal end side of the contact unit.

(18)

The tactile presentation apparatus according to any one of (13) to (17), in which the operation unit is rotatable by plus or minus 180 degrees or more from a reference state.

(19)

The tactile presentation apparatus according to (13), in which the operation unit includes therein a force sensor.

(20)

The tactile presentation apparatus according to (16), in which the third contact surface has a protruded part protruded along a rotational direction of the contact unit or a recessed part recessed along the rotational direction of the contact unit.

(21)

The tactile presentation apparatus according to any one of (13) to (20), in which wiring lines inside the vibration unit and the operation unit are electrically coupled to each other via a slip ring.

(22)

A tactile presentation system including:

a first information processor provided with a tactile presentation apparatus that presents to a user a first signal, as a tactile sense, related to a vibration of an operation target received from a slave apparatus, the first information processor functioning as a master apparatus that transmits to the slave apparatus a second signal in which a vibration noise estimated on a basis of the first signal is removed from force applied by the user; and a second information processor functioning as the slave apparatus that transmits to the first information processor the first signal measured when being driven on a basis of the second signal received from the first information processor.

REFERENCE NUMERALS LIST

10 master apparatus
50 slave apparatus
100 operation apparatus
110 operation unit 120 vibration unit
130 contact unit
140 installation unit
150 sensor unit
152 force sensor
170 signal processor
171 band limit section
172 DRI
173 A/D
174 inverse dynamics computation section
175 noise estimation section
178 adder
179 adder
180 storage section
190 high-level control section

The invention claimed is:

1. A tactile presentation apparatus comprising:
an operation structure operated by a user;
the operation structure includes a vibrator that generates a vibration corresponding to an operation target;
the operation structure includes a contact structure that transmits the vibration by the vibrator to the user; and
an installation structure that is coupled to the contact structure via an elastic body, wherein the installation structure is also coupled to the operation structure, wherein
the contact structure has a first contact surface to be in contact with a finger of the user,
the vibrator transmits the vibration to the finger of the user via the first contact surface,
the installation structure has a second contact surface with which the finger of the user comes into contact and an opening that penetrates between a side of the second contact surface and back side of the second contact surface, and
the contact structure is provided to be inserted through the opening from the back side of the second contact surface.

2. The tactile presentation apparatus according to claim 1, wherein the first contact surface and the second contact surface coincide or substantially coincide with each other in a vibration direction of the vibrator, with the vibrator being stopped.

3. The tactile presentation apparatus according to claim 2, wherein a shortest distance in the vibration direction between the first contact surface and an end of the second contact surface that forms the opening is within a range of a value corresponding to amplitude of the vibrator.

4. The tactile presentation apparatus according to claim 1, wherein the vibrator vibrates in a direction corresponding to a direction in which the elastic body expands and contracts.

5. The tactile presentation apparatus according to claim 4, wherein the vibrator vibrates in a direction coincident or substantially coincident with the direction in which the elastic body expands and contracts.

6. The tactile presentation apparatus according to claim 1, wherein the first contact surface has concavity and convexity.

7. The tactile presentation apparatus according to claim 1, wherein
the tactile presentation apparatus further comprises
a force sensor that measures force inputted to the operation structure, and
a signal processor that removes a component of the vibration presented by the vibrator from the force measured by the force sensor.

8. The tactile presentation apparatus according to claim 7, wherein the signal processor reduces an influence of a vibration noise correlated with force of the user by using an adaptive filter for the vibration.

9. The tactile presentation apparatus according to claim 7, wherein the signal processor uses a filter to remove, from the vibration, a frequency component other than a frequency component corresponding to a human tactile sense or a predetermined frequency component stored in advance.

10. The tactile presentation apparatus according to claim 1, wherein
the operation structure is rotatable along a predetermined rotational axis, and
the contact structure is rotatable along the predetermined rotational axis independently of the operation structure.

11. The tactile presentation apparatus according to claim 10, wherein the vibrator vibrates in a direction corresponding to a direction of the predetermined rotational axis.

12. The tactile presentation apparatus according to claim 10, wherein the vibrator, the contact structure, and the installation structure are provided on a distal end side of the operation structure.

13. The tactile presentation apparatus according to claim 10, wherein
an outer circumferential surface of the contact structure constitutes a third contact surface, and
the vibrator transmits the vibration to the user via the third contact surface.

14. The tactile presentation apparatus according to claim 13, wherein an outer circumference on distal end side of the contact structure is larger than an outer circumference on proximal end side of the contact structure.

15. The tactile presentation apparatus according to claim 10, wherein the operation structure includes therein a force sensor.

16. The tactile presentation apparatus according to claim 13, wherein the third contact surface has a protruded part protruded along a rotational direction of the contact structure or a recessed part recessed along the rotational direction of the contact structure.

17. The tactile presentation apparatus according to claim 10, wherein wiring lines inside the vibrator and the operation structure are electrically coupled to each other via a slip ring.

18. The tactile presentation apparatus according to claim 1, wherein the opening is circular or polygonal.

* * * * *